(12) United States Patent
Zeng et al.

(10) Patent No.: US 11,976,060 B2
(45) Date of Patent: May 7, 2024

(54) METHOD FOR PREPARING BETA-LACTAM DERIVATIVE

(71) Applicant: SOOCHOW UNIVERSITY, Suzhou (CN)

(72) Inventors: Runsheng Zeng, Suzhou (CN); Peng Shi, Suzhou (CN); Yingsheng Zhao, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 674 days.

(21) Appl. No.: 17/256,088

(22) PCT Filed: Sep. 4, 2019

(86) PCT No.: PCT/CN2019/104403
§ 371 (c)(1),
(2) Date: Dec. 24, 2020

(87) PCT Pub. No.: WO2020/114025
PCT Pub. Date: Jun. 11, 2020

(65) Prior Publication Data
US 2021/0276986 A1    Sep. 9, 2021

(30) Foreign Application Priority Data
Dec. 6, 2018 (CN) .......................... 201811487777.X

(51) Int. Cl.
| | | |
|---|---|---|
| *G03F 7/004* | (2006.01) |
| *B01J 31/18* | (2006.01) |
| *C07D 401/10* | (2006.01) |
| *C07D 405/14* | (2006.01) |
| *C07D 409/14* | (2006.01) |
| *C08F 212/08* | (2006.01) |
| *C08F 220/18* | (2006.01) |
| *C08F 220/38* | (2006.01) |
| *C08F 257/02* | (2006.01) |
| *C08K 5/04* | (2006.01) |
| *C09D 125/08* | (2006.01) |
| *C09D 133/14* | (2006.01) |
| *C09K 19/24* | (2006.01) |

(52) U.S. Cl.
CPC ........ *C07D 409/14* (2013.01); *B01J 31/1805* (2013.01); *C07D 401/10* (2013.01); *C07D 405/14* (2013.01); *B01J 2531/16* (2013.01)

(58) Field of Classification Search
CPC ........ G03F 7/004; G03G 9/0922; C08K 5/04; C08F 220/1806; C08F 220/1804; C08F 220/387; C08F 220/18; C08F 220/38; C08F 120/38; C08F 212/08; C08F 257/02; C09D 133/14; C09D 125/08; C09K 19/24; C09K 19/348; C09K 19/542
See application file for complete search history.

(56) References Cited

FOREIGN PATENT DOCUMENTS

| | | |
|---|---|---|
| CN | 103524486 A | 1/2014 |
| CN | 109369629 A | 2/2019 |

OTHER PUBLICATIONS

Shi et al., 2019, Chem Comm, 55, 10523-10526.*
Shi et al., "A practical copper-catalyzed approach to beta-lactams via radical carboamination of alkenyl carbonyl compounds", Chem. Commun. 2019, 55, 10523-10526 (Aug. 14, 2019).
Cui et al., "Iron-mediated remote C—H bond benzylation of 8-aminoquinoline amides", Tetrahedron Letters 58 (2017) 1912-1916 (Mar. 2, 2017).
Li et al., "Nickel-Catalyzed Addition-Type Alkenylation of Unactivated, Aliphatic C—H Bonds with Alkynes: A Concise Route to Polysubstituted gamma-Butyrolactones", Organic Letters, vol. 17, No. 10, 2546-2549 (Apr. 30, 2015).

* cited by examiner

Primary Examiner — Sun Jae Yoo
(74) Attorney, Agent, or Firm — SZDC Law PC

(57) ABSTRACT

The present invention relates to a method for preparing a β-lactam derivative, wherein a substituted N-quinoline-3-butenamide derivative is used as a substrate to react with a toluene derivative or a heterocyclic derivative at 90-150° C. in the presence of DTBP and a copper salt catalyst, to prepare a β-lactam derivative. According to the method of the present invention, a variety of β-lactam derivatives can be obtained with a high yield. The reaction of the present invention has mild reaction conditions, and simple reaction operation and post-treatment process, and is suitable for large-scale production.

8 Claims, No Drawings

METHOD FOR PREPARING BETA-LACTAM DERIVATIVE

This application is the National Stage Application of PCT/CN2019/104403, filed on Sep. 4, 2019, which claims priority to Chinese Patent Application No.: 201811487777.X, filed on Dec. 6, 2018, which is incorporated by reference for all purposes as if fully set forth herein.

FIELD OF THE INVENTION

The present invention relates to the technical field of preparation of organic compounds, and more particularly to a method for preparing a β-lactam derivative.

DESCRIPTION OF THE RELATED ART

β-lactam derivatives usually have significant biological and pharmacological activities, such as activities against viruses and Gram-negative bacilli. Therefore, the synthesis of β-lactam derivatives is of great importance.

So far, the synthesis of β-lactam derivatives is mainly involved in the following methods:

A method for preparing a β-lactam derivative through ring closing by oxidation is disclosed in *J. Am. Chem. Soc,* 1982, 104, 3233. A method for preparing a β-lactam derivative through ring closing by reduction is disclosed in *J. Org. Chem.* 1995, 60, 1276.

The methods for synthesizing β-lactam by C—H bond activation and metal catalysis are disclosed respectively in *Angewandte Chemie,* 2013, 52, 13588, *Angewandte Chemie* 2014, 53, 3496, and *Chem. Eur. J,* 2014, 20, 9530. However, the above methods have harsh reaction conditions, require the noble metal catalysts, and thus the cost is high. Moreover, the reaction with the activated group or the orienting group does not meet the requirements of atomic economy and environmental friendliness.

SUMMARY OF THE INVENTION

In order to overcome the shortcomings in the preparation of β-lactam derivatives in the prior art, such as low yield, expensive raw materials, harsh reaction conditions and environmental unfriendliness, the present invention provides a method for preparing a β-lactam derivative. The method has the advantages of readily available raw materials, high yield, mild reaction conditions, high generality as well as environmental friendliness.

The present invention provides a method for preparing a β-lactam derivative, which includes the following steps:

Reacting the substituted N-quinoline-3-butenamide derivative of Formula (1) and toluene or a toluene derivative of Formula (2) at 90-150° C. in the presence of di-tert-butyl peroxide (DTBP) and a copper salt catalyst, to give the β-lactam derivative of Formula (4), where the reaction route is as follows:

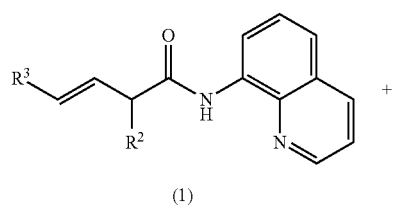

(1)

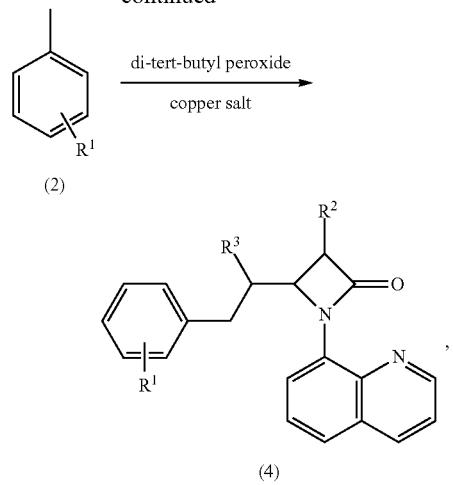

Or reacting the substituted N-quinoline-3-butenamide derivative of Formula (1) and a heterocyclic derivative of Formula (3) at 90-150° C. in the presence of di-tert-butyl peroxide and a copper salt catalyst, to give the β-lactam derivative of Formula (5), where the reaction route is as follows:

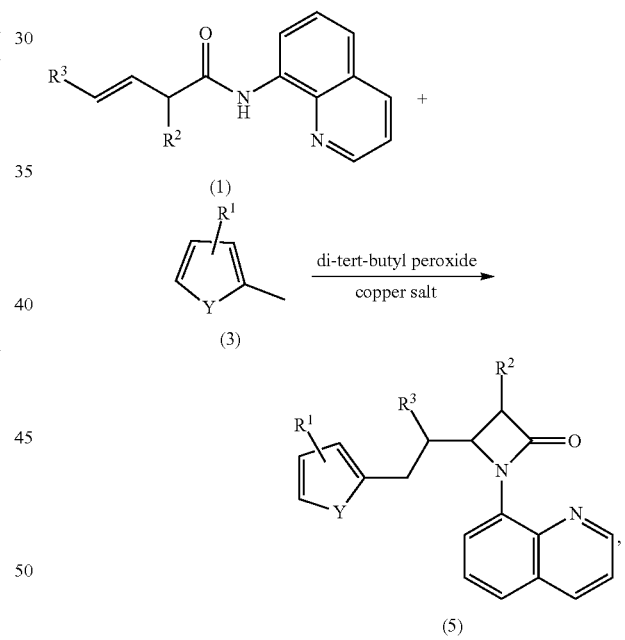

Wherein in Formulas (1)-(5), Y is an oxygen or sulfur atom;

$R^1$, $R^2$, and $R^3$ are selected such that $R^2$ and $R^3$ are hydrogen, and $R^1$ is hydrogen, methyl, halo or trifluoromethyl;

or $R^1$ and $R^2$ are hydrogen, and $R^3$ is C1-C6 alkyl or benzyl;

or $R^1$ and $R^3$ are hydrogen, and $R^2$ is C1-C6 alkyl, allyl, benzyl, phenylethyl, cyclopropylmethyl, or cyclobutylmethyl.

In the above preparation method, the toluene derivative of Formula (2) and the heterocyclic derivative of Formula (3) act as a reaction substrate and a reaction solvent in the absence of other organic solvents.

In an embodiment, when the substituted N-quinoline-3-butenamide derivative of Formula (1) reacts with the heterocyclic derivative of Formula (3), $R^2$ and $R^3$ are hydrogen, and $R^1$ is hydrogen, methyl, halo or trifluoromethyl. Preferably, $R^1$ is hydrogen.

In an embodiment, the copper salt catalyst is selected from the group consisting of cuprous bromide (CuBr), copper acetate (Cu(OAc)$_2$), cuprous chloride (CuCl), tetrakis(acetonitrile)copper hexafluorophosphate (Cu(CH$_3$CN)$_4$PF$_6$), copper trifluoromethanesulfonate, copper oxide, copper bromide (CuBr$_2$) and any combination thereof.

In an embodiment, the molar ratio of the substituted N-quinoline-3-butenamide derivative: di-tert-butyl peroxide:copper salt catalyst=1:1-3:0.05-0.2.

Preferably, the copper salt catalyst is tetrakis(acetonitrile) copper hexafluorophosphate.

Preferably, the molar ratio of the substituted N-quinoline-3-butenamide derivative: di-tert-butyl peroxide:copper salt catalyst=1:3:0.05-0.2. More preferably, the molar ratio of the substituted N-quinoline-3-butenamide derivative di-tert-butyl peroxide:copper salt catalyst=1:3:0.1.

In an embodiment, the reaction temperature is 130-150° C. Preferably, the reaction temperature is 130° C.

In an embodiment, the reaction system also comprises, in addition to toluene, the toluene derivative of Formula (2) or the heterocyclic derivative of Formula (3), an additional organic solvent.

Preferably, the organic solvent is selected from the group consisting of acetonitrile, tetrahydrofuran, N,N-dimethylformamide, isopropanol and any combination thereof.

Preferably, the reaction time is 8-10 h.

The present inventors found that the β-lactam derivative can be synthesized efficiently by initiating tandem radical cyclization. The present invention relates to a ring-forming reaction initiated by free radicals in presence of a copper salt catalyst. The reaction has mild reaction conditions and wide scope of application, and meets the requirements of green chemistry.

By means of the above solution, the present invention has the following advantages.

1. The present invention provides a novel system that utilizes the free radical reaction to synthesize a β-lactam derivative.

2. In the present invention, the substituted N-quinoline-3-butenamide derivative is used as a starting material, and a great variety of raw materials are easily available. In the method of the present invention, various products can be obtained, which can be used directly or used in further reactions.

3. The present invention provides a novel reaction with simple operations and post-treatment process and high yield, and thus is suitable for large-scale production.

The above description is only a summary of the technical solutions of the present invention. To make the technical means of the present invention clearer and implementable in accordance with the disclosure of the specification, the present invention will be described in detail hereinafter with reference to the preferred embodiments.

DETAILED DESCRIPTION OF THE PREFERRED EMBODIMENTS

The specific embodiments of the present invention will be described in further detail with reference to examples. The following examples are intended to illustrate the present invention, instead of limiting the scope of the present invention.

Example 1: Synthesis of 4-phenethyl-1-(quinolin-8-yl)azetidin-2-one

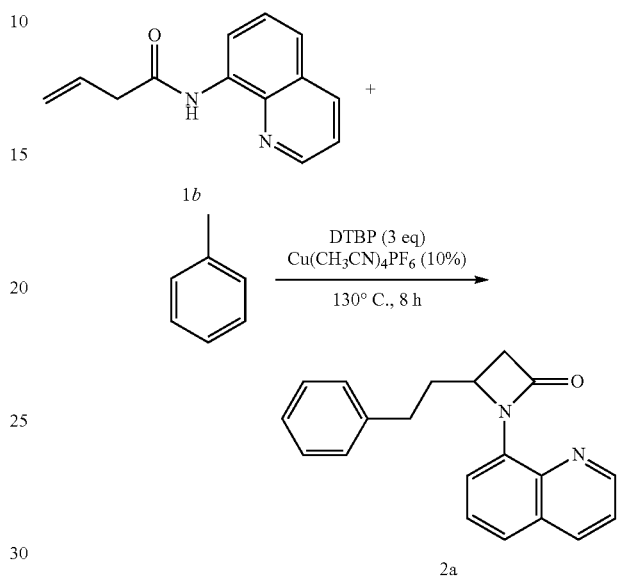

(1) N-(8-quinolyl)-3-butenamide 1a (0.042 g, 0.2 mmol), and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 92%.

(2) N-(8-quinolyl)-3-butenamide 1a (0.042 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 110° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 80%.

(3) N-(8-quinolyl)-3-butenamide 1a (0.042 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 140° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 90%.

(4) N-(8-quinolyl)-3-butenamide 1a (0.042 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 90° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 22%.

(5) N-(8-quinolyl)-3-butenamide 1a (0.042 g, 0.2 mmol) and CuBr₂ (0.005 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 56%.

(6) N-(8-quinolyl)-3-butenamide 1a (0.042 g, 0.2 mmol) and Cu(OAc)₂ (0.004 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 18%.

(7) N-(8-quinolyl)-3-butenamide 1a (0.042 g, 0.2 mmol) and CuBr (0.003 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2a. The yield after separation was 20%.

2a: $^1$H NMR (400 MHz, CDCl₃) δ 8.78 (dd, J=4.1, 1.8 Hz, 1H), 8.27 (dd, J=7.5, 1.4 Hz, 1H), 8.11 (dd, J=8.3, 1.7 Hz, 1H), 7.57 (dd, J=8.2, 1.4 Hz, 1H), 7.54-7.47 (m, 1H), 7.39 (dd, J=8.3, 4.1 Hz, 1H), 7.29-7.21 (m, 2H), 7.20-7.15 (m, 1H), 7.14-7.10 (m, 2H), 5.20 (ddd, J=11.8, 5.6, 2.9 Hz, 1H), 3.32 (dd, J=15.0, 5.3 Hz, 1H), 2.82 (dd, J=15.0, 2.6 Hz, 1H), 2.74-2.62 (m, 2H), 2.37 (tdd, J=9.1, 7.2, 3.3 Hz, 1H), 1.84 (dtd, J=13.3, 8.7, 6.4 Hz, 1H); $^{13}$C NMR (101 MHz, CDCl₃) δ 166.46 (s), 148.92 (s), 141.10 (s), 140.65 (s), 136.03 (s), 133.61 (s), 128.99 (s), 128.38 (s), 128.29 (s), 126.70 (s), 126.02 (s), 124.01 (s), 121.63 (s), 121.32 (s), 56.11 (s), 43.12 (s), 35.24 (s), 31.63 (s). HRMS(ESI-TOF) Calcd for C₂₀H₁₉N₂O [M+H]⁺: 303.1497, found: 303.1512.

Example 2

Synthesis of 4-(3-methylphenethyl)-1-(quinolin-8-yl)azetidin-2-one

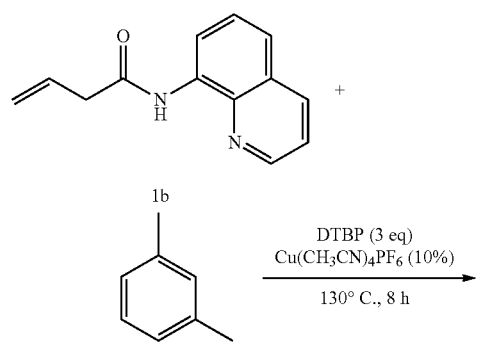

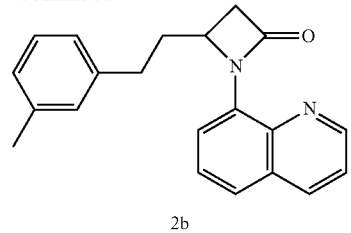

2b

N-(8-quinolyl)-3-butenamide 1b (0.042 g, 0.2 mmol) and Cu(CH₃CN)₄PF₆ (0.008 g, 0.02 mmol) were weighed and dissolved in m-xylene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2b. The yield after separation was 86%.

2b: $^1$H NMR (400 MHz, CDCl₃) δ 8.80 (dd, J=4.1, 1.8 Hz, 1H), 8.28 (dd, J=7.5, 1.4 Hz, 1H), 8.11 (dd, J=8.3, 1.8 Hz, 1H), 7.57 (dd, J=8.2, 1.4 Hz, 1H), 7.54-7.46 (m, 1H), 7.39 (dd, J=8.3, 4.1 Hz, 1H), 7.18-7.12 (m, 1H), 7.00 (d, J=7.6 Hz, 1H), 6.93 (d, J=6.5 Hz, 2H), 5.21 (ddd, J=11.7, 5.7, 3.0 Hz, 1H), 3.33 (dd, J=15.0, 5.3 Hz, 1H), 2.84 (dd, J=15.0, 2.6 Hz, 1H), 2.69-2.63 (m, 2H), 2.41-2.34 (m, 1H), 2.31 (s, 2H), 1.93-1.78 (m, 1H); $^{13}$C NMR (101 MHz, CDCl₃) δ 166.05 (s), 148.48 (s), 140.59 (s), 140.22 (s), 137.45 (s), 135.56 (s), 133.18 (s), 128.62 (s), 128.53 (s), 127.83 (s), 126.28 (s), 126.23 (s), 124.83 (s), 123.58 (s), 121.19 (s), 120.86 (s), 55.70 (s), 42.65 (s), 34.78 (s), 31.05 (s), 20.92 (s); HRMS Calcd for C₂₁H₂₁N₂O [M+H]⁺: 317.1654, Found: 317.1669.

Example 3

Synthesis of 4-(4-methylphenethyl)-1-(quinolin-8-yl)azetidin-2-one

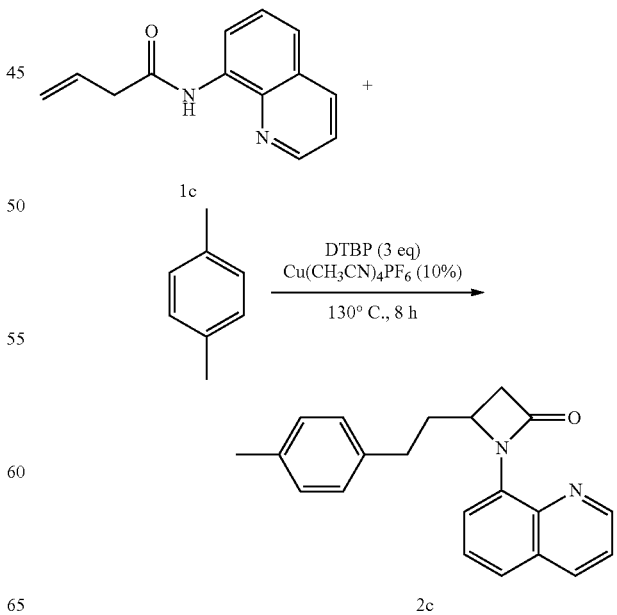

N-(8-quinolyl)-3-butenamide 1c (0.042 g, 0.2 mmol) and Cu(CH$_3$CN)$_4$PF$_6$ (0.008 g, 0.02 mmol) were weighed and dissolved in p-xylene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2c. The yield after separation was 62%.

2c: $^1$H NMR (400 MHz, CDCl$_3$) δ 8.80 (dd, J=4.1, 1.8 Hz, 1H), 8.26 (dd, J=7.5, 1.4 Hz, 1H), 8.12 (dd, J=8.3, 1.7 Hz, 1H), 7.58 (dd, J=8.2, 1.4 Hz, 1H), 7.54-7.47 (m, 1H), 7.39 (dd, J=8.3, 4.1 Hz, 1H), 7.07 (d, J=7.9 Hz, 2H), 7.01 (d, J=8.1 Hz, 2H), 5.19 (ddd, J=11.8, 5.7, 3.0 Hz, 1H), 3.32 (dd, J=15.0, 5.3 Hz, 1H), 2.82 (dd, J=15.0, 2.6 Hz, 1H), 2.69-2.60 (m, 2H), 2.45-2.32 (m, 1H), 2.30 (s, 3H), 1.90-1.76 (m, 1H); $^{13}$C NMR (101 MHz, CDCl$_3$) δ 166.55 (s), 148.95 (s), 140.68 (s), 138.00 (s), 136.04 (s), 135.47 (s), 133.64 (s), 129.06 (s), 129.00 (s), 128.15 (s), 126.70 (s), 124.04 (s), 121.67 (s), 121.33 (s), 56.18 (s), 43.09 (s), 35.30 (s), 31.15 (s), 21.00 (s); HRMS Calcd for C$_{21}$H$_{21}$N$_2$O [M+H]$^+$: 317.1654, Found: 317.1668.

Example 4

Synthesis of 4-(2-methylphenethyl)-1-(quinolin-8-yl)azetidin-2-one

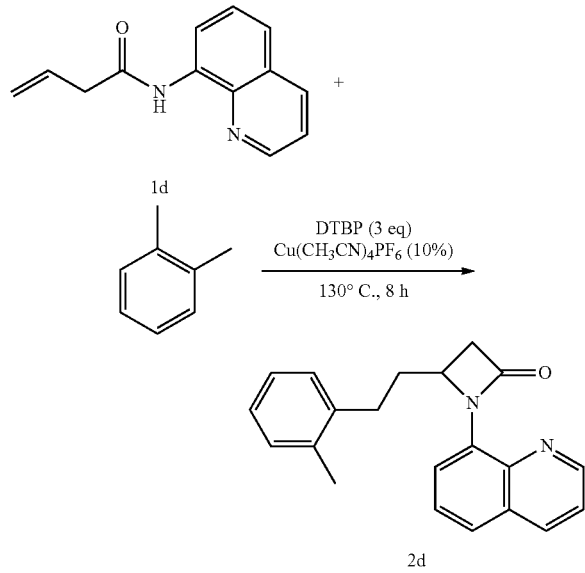

N-(8-quinolyl)-3-butenamide 1d (0.042 g, 0.2 mmol) and Cu(CH$_3$CN)$_4$PF$_6$ (0.008 g, 0.02 mmol) were weighed and dissolved in o-xylene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2d. The yield after separation was 80%.

2d: $^1$H NMR (400 MHz, CDCl$_3$) δ 8.79 (dd, J=4.1, 1.8 Hz, 1H), 8.30 (dd, J=7.5, 1.5 Hz, 1H), 8.11 (dd, J=8.3, 1.8 Hz, 1H), 7.57 (dd, J=8.2, 1.4 Hz, 1H), 7.54-7.49 (m, 1H), 7.39 (dd, J=8.3, 4.1 Hz, 1H), 7.11-7.05 (m, 4H), 5.25 (ddd, J=11.6, 5.7, 3.0 Hz, 1H), 3.37 (dd, J=15.0, 5.3 Hz, 1H), 2.88 (dd, J=15.0, 2.6 Hz, 1H), 2.66 (t, J=8.0 Hz, 2H), 2.36-2.28 (m, 1H), 2.17 (s, 3H), 1.85-1.75 (m, 1H). $^{13}$C NMR (101 MHz, CDCl$_3$) δ 166.02 (s), 148.43 (s), 140.12 (s), 138.84 (s), 135.59 (s), 135.24 (s), 133.21 (s), 129.75 (s), 128.53 (s), 128.17 (s), 126.26 (s), 125.70 (s), 125.54 (s), 123.54 (s), 121.08 (s), 120.86 (s), 55.80 (s), 42.66 (s), 33.70 (s), 28.45 (s), 18.60 (s). 43.09 (s), 35.30 (s), 31.15 (s), 21.00 (s); HRMS Calcd for C$_{21}$H$_{21}$N$_2$O [M+H]$^+$; 317.1654, Found: 317.1693.

Example 5

Synthesis of 4-(2-chlorophenethyl)-1-(quinolin-8-yl)azetidin-2-one

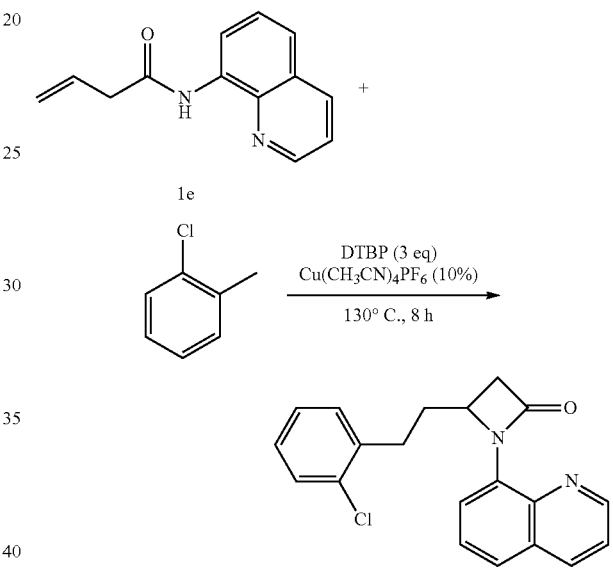

N-(8-quinolyl)-3-butenamide 1e (0.042 g, 0.2 mmol) and Cu(CH$_3$CN)$_4$PF$_6$ (0.008 g, 0.02 mmol) were weighed and dissolved in o-chlorotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2e. The yield after separation was 83%.

2e: $^1$H NMR (400 MHz, CDCl$_3$) δ 8.77 (dd, J=4.1, 1.8 Hz, 1H), 8.28 (dd, J=7.5, 1.4 Hz, 1H), 8.11 (dd, J=8.3, 1.7 Hz, 1H), 7.57 (dd, J=8.1, 1.4 Hz, 1H), 7.52-7.47 (m, 1H), 7.39 (dd, J=8.3, 4.1 Hz, 1H), 7.31-7.28 (m, 1H), 7.15-7.08 (m, 3H), 5.23 (ddd, J=11.8, 5.6, 2.9 Hz, 1H), 3.36 (dd, J=15.0, 5.3 Hz, 1H), 2.88 (dd, J=15.0, 2.6 Hz, 1H), 2.79 (dd, J=8.7, 6.8 Hz, 2H), 2.36 (dtd, J=11.0, 8.0, 3.3 Hz, 1H), 1.90-1.78 (m, 1H). $^{13}$C NMR (101 MHz, CDCl$_3$) δ 165.94 (s), 148.42 (s), 140.08 (s), 138.30 (s), 135.52 (s), 133.36 (s), 133.18 (s), 129.78 (s), 129.02 (s), 128.50 (s), 127.07 (s), 126.33 (s), 126.22 (s), 123.46 (s), 120.99 (s), 120.83 (s), 55.58 (s), 42.68 (s), 33.30 (s), 28.99 (s); HRMS Calcd for C$_{20}$H$_{18}$ClN$_2$O [M+H]$^+$: 337.1108, Found: 317.1122.

Example 6

Synthesis of 4-(3-chlorophenethyl)-1-(quinolin-8-yl)azetidin-2-one

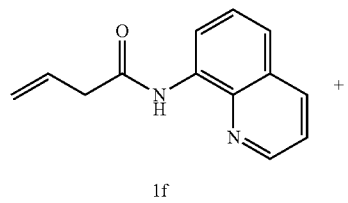

1f

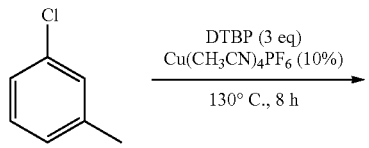

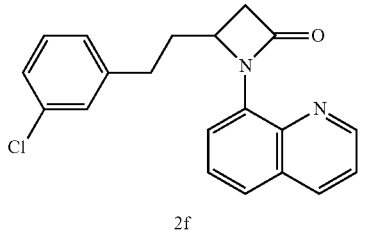

2f

N-(8-quinolyl)-3-butenamide 1f (0.042 g, 0.2 mmol) and Cu(CH$_3$CN)$_4$PF$_6$ (0.008 g, 0.02 mmol) were weighed and dissolved in m-chlorotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2f. The yield after separation was 82%.

2f: $^1$H NMR (400 MHz, CDCl$_3$) δ 8.79 (dd, J=4.1, 1.8 Hz, 1H), 8.26 (dd, J=7.5, 1.4 Hz, 1H), 8.13 (dd, J=8.3, 1.8 Hz, 1H), 7.58 (dd, J=8.2, 1.4 Hz, 1H), 7.54-7.47 (m, 1H), 7.41 (dd, J=8.3, 4.1 Hz, 1H), 7.17 (dd, J=12.3, 5.0 Hz, 2H), 7.12 (s, 1H), 7.01-6.97 (m, 1H), 5.19 (ddd, J=11.8, 5.7, 3.0 Hz, 1H), 3.33 (dd, J=15.0, 5.3 Hz, 1H), 2.82 (dd, J=15.0, 2.6 Hz, 1H), 2.75-2.59 (m, 2H), 2.42-2.31 (m, 1H), 1.84 (dtd, J=13.4, 8.8, 6.0 Hz, 1H). $^{13}$C NMR (101 MHz, CDCl$_3$) δ 166.24 (s), 149.00 (s), 143.08 (s), 140.56 (s), 136.07 (s), 134.15 (s), 133.53 (s), 129.61 (s), 129.00 (s), 128.35 (s), 126.72 (s), 126.58 (s), 126.23 (s), 124.05 (s), 121.57 (s), 121.38 (s), 55.81 (s), 43.09 (s), 34.84 (s), 31.28 (s); HRMS Calcd for C20H17ClN2ONa [M+Na]$^+$: 359.0927, Found: 359.0939.

Example 7

Synthesis of 4-(4-chlorophenethyl)-1-(quinolin-8-yl)azetidin-2-one

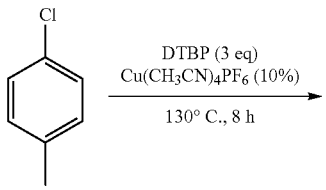

1g

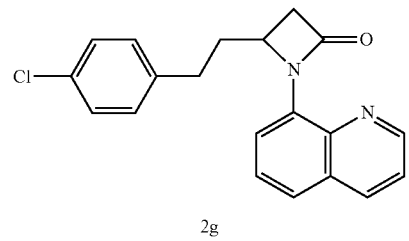

2g

N-(8-quinolyl)-3-butenamide 1g (0.042 g, 0.2 mmol) and Cu(CH$_3$CN)$_4$PF$_6$ (0.008 g, 0.02 mmol) were weighed and dissolved in p-chlorotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2g. The yield after separation was 83%.

2g: $^1$H NMR (400 MHz, CDCl$_3$) δ 8.76 (dd, J=4.1, 1.8 Hz, 1H), 8.24 (dd, J=7.5, 1.4 Hz, 1H), 8.12 (dd, J=8.3, 1.7 Hz, 1H), 7.58 (dd, J=8.2, 1.3 Hz, 1H), 7.52-7.47 (m, 1H), 7.40 (dd, J=8.3, 4.1 Hz, 1H), 7.22-7.18 (m, 2H), 7.03 (d, J=8.4 Hz, 2H), 5.18 (ddd, J=11.7, 5.7, 3.0 Hz, 1H), 3.32 (dd, J=15.0, 5.3 Hz, 1H), 2.81 (dd, J=15.0, 2.6 Hz, 1H), 2.69-2.58 (m, 2H), 2.33 (tdd, J=9.2, 7.3, 3.3 Hz, 1H), 1.83 (dtd, J=13.4, 8.7, 6.3 Hz, 2H). $^{13}$C NMR (101 MHz, CDCl$_3$) δ 165.82 (s), 148.44 (s), 140.12 (s), 139.04 (s), 135.60 (s), 133.05 (s), 131.25 (s), 129.14 (s), 128.52 (s), 127.97 (s), 126.24 (s), 123.59 (s), 121.14 (s), 120.88 (s), 55.42 (s), 42.57 (s), 34.58 (s), 30.46 (s); HRMS Calcd for C$_{20}$H$_{18}$ClN$_2$O [M+H]$^+$: 337.1108, Found: 337.1118.

Example 8

Synthesis of 4-(2-(furan-2-yl)ethyl)-1-(quinolin-8-yl)azetidin-2-one

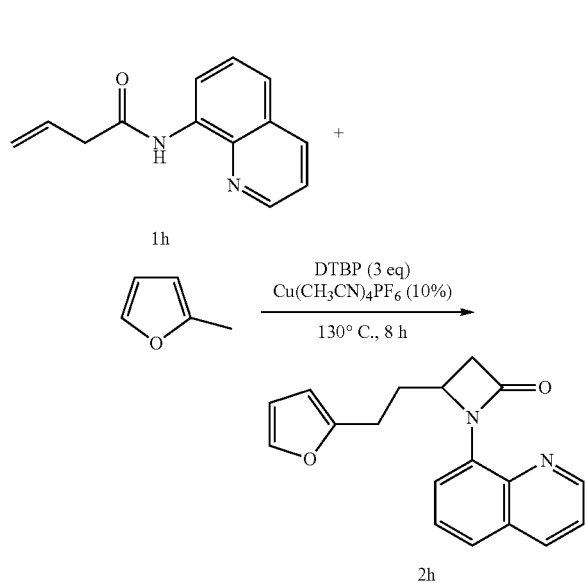

N-(8-quinolyl)-3-butenamide 1h (0.042 g, 0.2 mmol) and Cu(CH₃CN)₄PF₆ (0.008 g, 0.02 mmol) were weighed and dissolved in 2-methylfuran (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2h. The yield after separation was 80%.

2h: $^1$H NMR (400 MHz, CDCl₃) δ 8.82 (dd, J=4.1, 1.8 Hz, 1H), 8.25 (dd, J=7.5, 1.4 Hz, 1H), 8.13 (dd, J=8.3, 1.8 Hz, 1H), 7.58 (dd, J=8.2, 1.4 Hz, 1H), 7.54-7.48 (m, 1H), 7.40 (dd, J=8.3, 4.1 Hz, 1H), 7.27 (dd, J=1.8, 0.7 Hz, 1H), 6.26 (dd, J=3.1, 1.9 Hz, 1H), 5.98 (dd, J=3.1, 0.8 Hz, 1H), 5.23 (ddd, J=11.7, 5.7, 3.0 Hz, 1H), 3.31 (dd, J=15.1, 5.3 Hz, 1H), 2.76 (dd, J=15.1, 2.6 Hz, 1H), 2.70 (t, J=7.5 Hz, 2H), 2.41-2.33 (m, 1H), 1.93-1.83 (m, 1H). $^{13}$C NMR (101 MHz, CDCl₃) δ 165.89 (s), 154.26 (s), 148.50 (s), 140.48 (s), 140.18 (s), 135.56 (s), 133.08 (s), 128.53 (s), 126.22 (s), 123.57 (s), 121.15 (s), 120.86 (s), 109.73 (s), 104.73 (s), 55.47 (s), 42.56 (s), 31.62 (s), 23.51 (s); HRMS Calcd for C₁₈H₁₇N₂O₂ [M+H]⁺: 293.1290, Found: 293.1300.

Example 9

Synthesis of 1-(quinolin-8-yl)-4-(2-(thiophen-2-yl)ethyl)azetidin-2-one

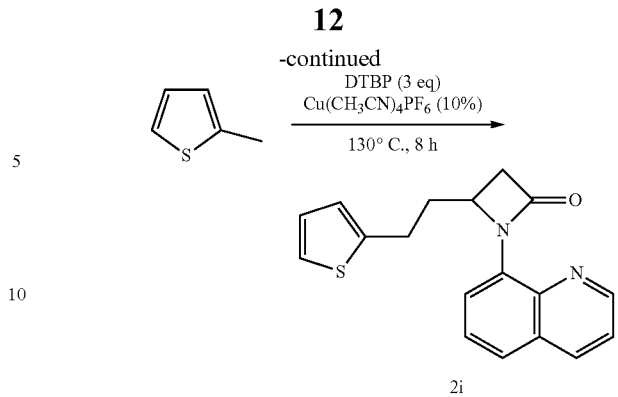

N-(8-quinolyl)-3-butenamide 1i (0.042 g, 0.2 mmol) and Cu(CH₃CN)₄PF₆ (0.008 g, 0.02 mmol) were weighed and dissolved in 2-methylthiophene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2i. The yield after separation was 65%.

2i: $^1$H NMR (400 MHz, CDCl₃) δ 8.81 (dd, J=4.1, 1.7 Hz, 1H), 8.26 (dd, J=7.5, 1.4 Hz, 1H), 8.13 (dd, J=8.3, 1.7 Hz, 1H), 7.58 (dd, J=8.2, 1.3 Hz, 1H), 7.54-7.48 (m, 1H), 7.40 (dd, J=8.3, 4.1 Hz, 1H), 7.10 (dd, J=5.1, 1.1 Hz, 1H), 6.89 (dd, J=5.1, 3.4 Hz, 1H), 6.76 (dd, J=2.3, 1.0 Hz, 1H), 5.25 (ddd, J=11.7, 5.7, 3.0 Hz, 1H), 3.33 (dd, J=15.0, 5.3 Hz, 1H), 2.91 (t, J=7.6 Hz, 2H), 2.83 (dd, J=15.0, 2.6 Hz, 1H), 2.43 (dtd, J=11.5, 8.0, 3.4 Hz, 1H), 1.92 (ddt, J=13.4, 9.1, 7.3 Hz, 1H). $^{13}$C NMR (101 MHz, CDCl₃) δ 8.81 (dd, J=4.1, 1.7 Hz, 1H), 8.26 (dd, J=7.5, 1.4 Hz, 1H), 8.13 (dd, J=8.3, 1.7 Hz, 1H), 7.58 (dd, J=8.2, 1.3 Hz, 1H), 7.54-7.48 (m, 1H), 7.40 (dd, J=8.3, 4.1 Hz, 1H), 7.10 (dd, J=5.1, 1.1 Hz, 1H), 6.89 (dd, J=5.1, 3.4 Hz, 1H), 6.76 (dd, J=2.3, 1.0 Hz, 1H), 5.25 (ddd, J=11.7, 5.7, 3.0 Hz, 1H), 3.33 (dd, J=15.0, 5.3 Hz, 1H), 2.91 (t, J=7.6 Hz, 2H), 2.83 (dd, J=15.0, 2.6 Hz, 1H), 2.43 (dtd, J=11.5, 8.0, 3.4 Hz, 1H), 1.92 (ddt, J=13.4, 9.1, 7.3 Hz, 1H). 23.51; HRMS Calcd for C₁₈H₁₇N₂OS [M+H]⁺: 309.1062, Found: 309.1077.

Example 10

Synthesis of 4-(3-fluorophenethyl)-1-(quinolin-8-yl)azetidin-2-one

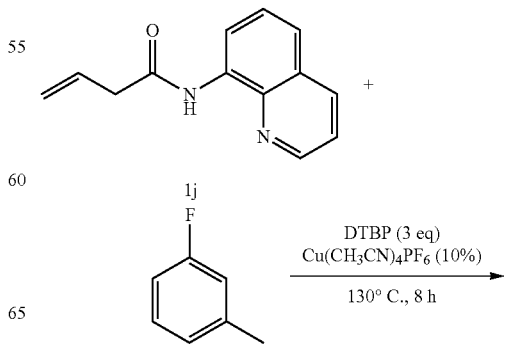

-continued

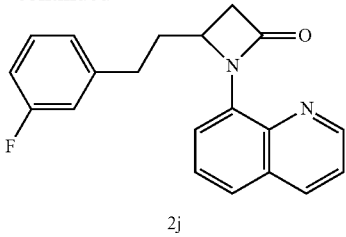

2j

N-(8-quinolyl)-3-butenamide 1j (0.042 g, 0.2 mmol) and Cu(CH₃CN)₄PF₆ (0.008 g, 0.02 mmol) were weighed and dissolved in m-fluorotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2j. The yield after separation was 64%.

2j: $^1$H NMR (400 MHz, CDCl₃) δ 8.79 (dd, J=4.1, 1.8 Hz, 1H), 8.26 (dd, J=7.5, 1.4 Hz, 1H), 8.12 (dd, J=8.4, 1.7 Hz, 1H), 7.58 (dd, J=8.2, 1.3 Hz, 1H), 7.53-7.47 (m, 1H), 7.40 (dd, J=8.3, 4.1 Hz, 1H), 7.20 (td, J=7.8, 6.2 Hz, 1H), 6.91-6.82 (m, 3H), 5.19 (ddd, J=11.8, 5.6, 3.0 Hz, 1H), 3.32 (dd, J=15.0, 5.3 Hz, 1H), 2.81 (dd, J=15.0, 2.6 Hz, 1H), 2.75-2.62 (m, 2H), 2.45-2.31 (m, 1H), 1.90-1.77 (m, 1H). $^{19}$F NMR (376 MHz, CDCl₃) δ −113.64 (s). $^{13}$C NMR (101 MHz, CDCl₃) δ 165.81 (s), 163.64 (s), 161.20 (s), 148.49 (s), 143.14 (d, J=7.2 Hz), 140.10 (s), 135.60 (s), 133.07 (s), 129.30 (d, J=8.4 Hz), 128.53 (s), 126.24 (s), 123.73-123.07 (m), 121.09 (s), 120.90 (s), 114.61 (d, J=21.0 Hz), 112.42 (d, J=20.9 Hz), 55.38 (s), 42.59 (s), 34.33 (s), 30.84 (s); HRMS Calcd for C₂₀H₁₈FN₂O [M+H]⁺: 321.1403, Found: 321.1400.

Example 11

Synthesis of 4-(2-fluorophenethyl)-1-(quinolin-8-yl)azetidin-2-one

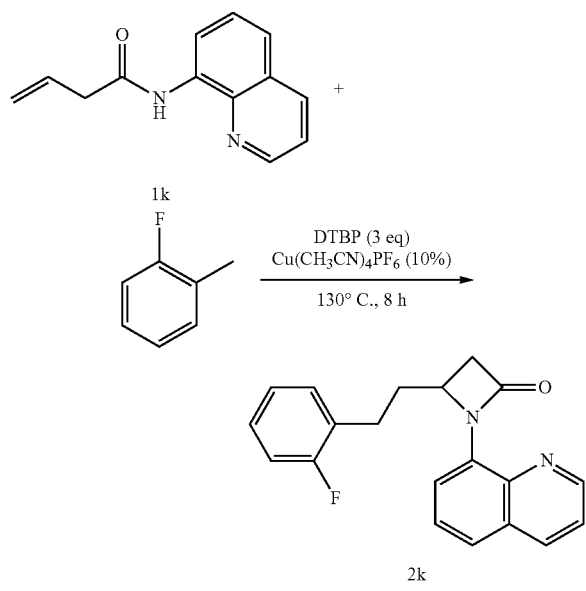

N-(8-quinolyl)-3-butenamide 1k (0.042 g, 0.2 mmol) and Cu(CH₃CN)₄PF₆ (0.008 g, 0.02 mmol) were weighed and dissolved in o-fluorotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2k. The yield after separation was 82%.

2k: $^1$H NMR (400 MHz, CDCl₃) δ 8.73 (dd, J=4.1, 1.8 Hz, 1H), 8.27 (dd, J=7.5, 1.4 Hz, 1H), 8.10 (dd, J=8.3, 1.8 Hz, 1H), 7.55 (dd, J=8.2, 1.4 Hz, 1H), 7.52-7.45 (m, 1H), 7.37 (dd, J=8.3, 4.1 Hz, 1H), 7.19-7.08 (m, 2H), 7.04-6.92 (m, 2H), 5.19 (ddd, J=12.1, 5.5, 2.9 Hz, 1H), 3.33 (dd, J=15.0, 5.3 Hz, 1H), 2.83 (dd, J=15.1, 2.6 Hz, 1H), 2.71 (t, J=7.7 Hz, 2H), 2.37 (dtd, J=11.3, 8.0, 3.2 Hz, 1H), 1.89-1.73 (m, 2H). $^{19}$F NMR (376 MHz, CDCl₃) δ −118.68 (s). $^{13}$C NMR (101 MHz, CDCl₃) δ 165.94 (s), 161.79 (s), 159.36 (s), 148.40 (s), 140.07 (s), 135.52 (s), 133.13 (s), 129.98 (d, J=4.9 Hz), 128.49 (s), 127.60 (s), 127.45 (s), 127.32 (d, J=8.1 Hz), 126.20 (s), 123.50 (d, J=4.0 Hz), 120.92 (d, J=16.5 Hz), 114.74 (d, J=22.1 Hz), 55.56 (s), 42.67 (s), 33.57 (s), 24.46 (d, J=2.6 Hz); HRMS Calcd for C₂₀H₁₈FN₂O [M+H]⁺: 321.1403, Found: 321.1398.

Example 12

Synthesis of 4-(2-bromophenethyl)-1-(quinolin-8-yl)azetidin-2-one

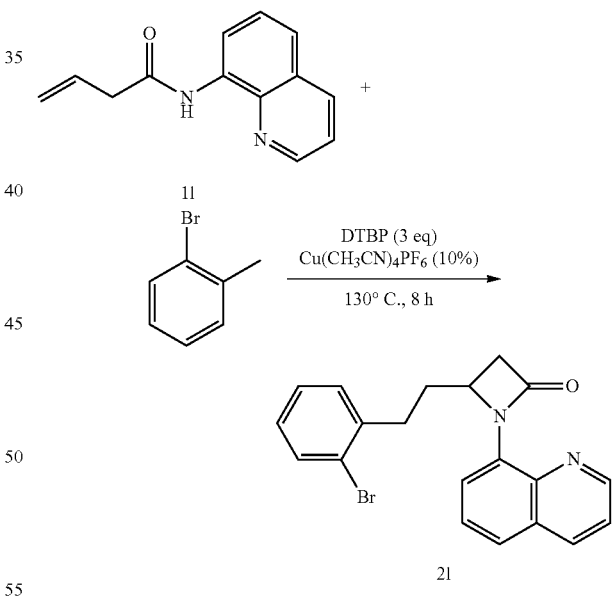

N-(8-quinolyl)-3-butenamide 1l (0.042 g, 0.2 mmol) and Cu(CH₃CN)₄PF₆ (0.008 g, 0.02 mmol) were weighed and dissolved in o-bromotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2l. The yield after separation was 82%.

2l: $^1$H NMR (400 MHz, CDCl₃) δ 8.77 (dd, J=4.1, 1.8 Hz, 1H), 8.28 (dd, J=7.5, 1.5 Hz, 1H), 8.10 (dd, J=8.3, 1.8 Hz,

1H), 7.56 (dd, J=8.2, 1.4 Hz, 1H), 7.52-7.45 (m, 2H), 7.38 (dd, J=8.3, 4.1 Hz, 1H), 7.15 (ddd, J=9.6, 7.4, 1.5 Hz, 2H), 7.05-6.99 (m, 1H), 5.24 (ddd, J=11.7, 5.6, 2.9 Hz, 1H), 3.36 (dd, J=15.0, 5.3 Hz, 1H), 2.90 (dd, J=15.0, 2.6 Hz, 1H), 2.78 (dd, J=9.1, 7.1 Hz, 2H), 2.34 (dtd, J=9.0, 7.9, 3.3 Hz, 1H), 1.87-1.80 (m, 1H). $^{13}$C NMR (101 MHz, CDCl$_3$) δ 165.95 (s), 148.46 (s), 140.09 (s), 140.00 (s), 135.53 (s), 133.19 (s), 132.34 (s), 129.77 (s), 128.50 (s), 127.33 (s), 127.00 (s), 126.22 (s), 123.83 (s), 123.49 (s), 121.01 (s), 120.84 (s), 55.53 (s), 42.68 (s), 33.48 (s), 31.55 (s); HRMS Calcd for C$_{20}$H$_{18}$BrN$_2$O [M+H]$^+$: 381.0603, Found: 381.0607.

Example 13

Synthesis of 4-(2-iodophenethyl)-1-(quinolin-8-yl) azetidin-2-one

Example 14

Synthesis of 4-(3-iodophenethyl)-1-(quinolin-8-yl) azetidin-2-one

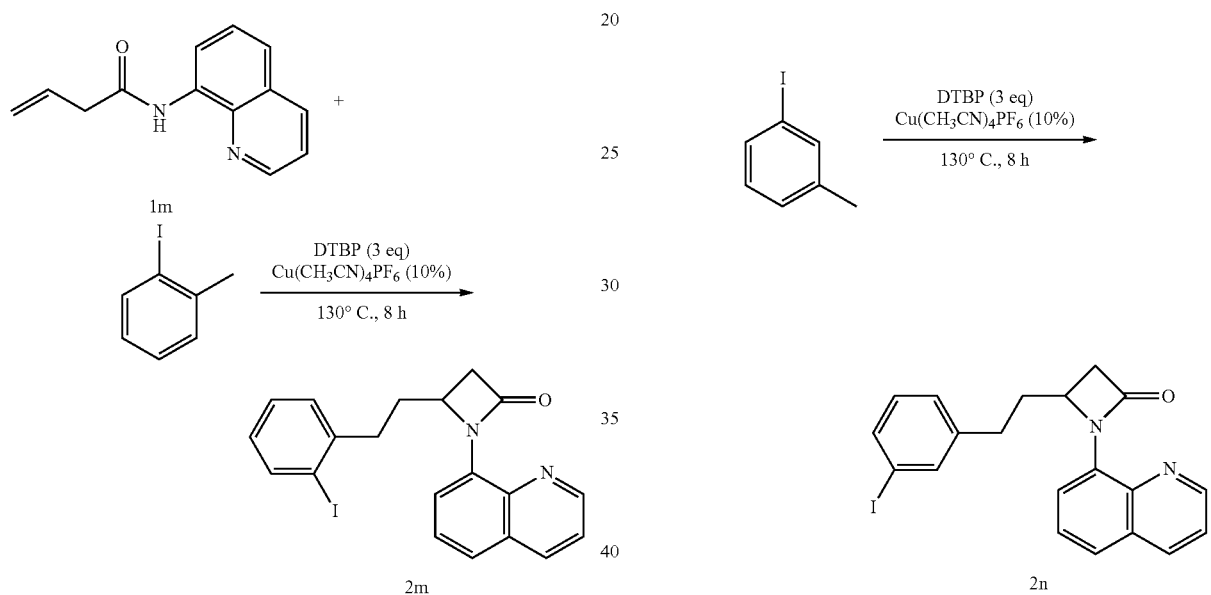

N-(8-quinolyl)-3-butenamide 1m (0.042 g, 0.2 mmol) and Cu(CH$_3$CN)$_4$PF$_6$ (0.008 g, 0.02 mmol) were weighed and dissolved in o-iodotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2m. The yield after separation was 80%.

2m: $^1$H NMR (400 MHz, CDCl$_3$) δ 8.79 (dt, J=12.6, 6.3 Hz, 1H), 8.29 (dd, J=7.5, 1.4 Hz, 1H), 8.10 (dd, J=8.3, 1.7 Hz, 1H), 7.75 (dd, J=7.9, 1.1 Hz, 1H), 7.56 (dd, J=8.1, 1.4 Hz, 1H), 7.52-7.45 (m, 1H), 7.38 (dd, J=8.3, 4.1 Hz, 1H), 7.21 (td, J=7.5, 1.1 Hz, 1H), 7.12 (dd, J=7.6, 1.6 Hz, 1H), 6.84 (td, J=7.7, 1.7 Hz, 1H), 5.26 (ddd, J=11.6, 5.7, 3.0 Hz, 1H), 3.37 (dd, J=15.0, 5.3 Hz, 1H), 2.94 (dd, J=15.0, 2.6 Hz, 1H), 2.83-2.65 (m, 1H), 2.41-2.17 (m, 1H), 1.89-1.73 (m, 1H). $^{13}$C NMR (101 MHz, CDCl$_3$) δ 165.93 (s), 148.53 (s), 143.25 (s), 140.13 (s), 139.03 (s), 135.54 (s), 133.21 (s), 128.82 (s), 128.53 (s), 127.92 (s), 127.46 (s), 126.24 (s), 123.50 (s), 121.05 (s), 120.85 (s), 99.84 (s), 55.46 (s), 42.71 (s), 36.20 (s), 33.83 (s); HRMS Calcd for C$_{20}$H$_{18}$BrN$_2$O [M+H]$^+$: 429.0464, Found: 429.0474.

N-(8-quinolyl)-3-butenamide in (0.042 g, 0.2 mmol) and Cu(CH$_3$CN)$_4$PF$_6$ (0.008 g, 0.02 mmol) were weighed and dissolved in m-iodotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2n. The yield after separation was 62%.

2n: $^1$H NMR (400 MHz, CDCl$_3$) δ 8.79 (dd, J=4.1, 1.8 Hz, 1H), 8.24 (dd, J=7.5, 1.4 Hz, 1H), 8.13 (dd, J=8.4, 1.7 Hz, 1H), 7.58 (dd, J=8.2, 1.4 Hz, 1H), 7.54-7.46 (m, 3H), 7.41 (dd, J=8.3, 4.1 Hz, 1H), 7.07 (d, J=8.0 Hz, 1H), 6.98 (t, J=7.7 Hz, 1H), 5.18 (ddd, J=11.8, 5.7, 3.0 Hz, 1H), 3.32 (dd, J=15.0, 5.3 Hz, 1H), 2.81 (dd, J=15.0, 2.6 Hz, 1H), 2.70-2.52 (m, 2H), 2.34 (dddd, J=12.7, 9.2, 7.2, 3.3 Hz, 1H), 1.82 (dtd, J=13.4, 8.8, 5.9 Hz, 1H). $^{13}$C NMR (101 MHz, CDCl$_3$) δ 166.26 (s), 149.06 (s), 143.53 (s), 140.57 (s), 137.23 (s), 136.08 (s), 135.13 (s), 133.50 (s), 130.11 (s), 129.00 (s), 127.68 (s), 126.71 (s), 124.09 (s), 121.59 (s), 121.40 (s), 94.51 (s), 55.82 (s), 43.09 (s), 34.91 (s), 31.17 (s); HRMS Calcd for C$_{20}$H$_{18}$BrN$_2$O [M+H]$^+$: 429.0464, Found: 429.0472.

Example 15

Synthesis of 4-(4-iodophenethyl)-1-(quinolin-8-yl)azetidin-2-one

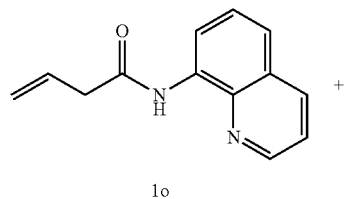

1o

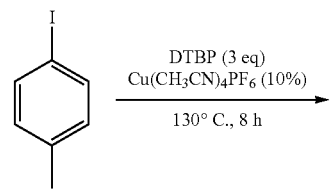

2o

Example 16

Synthesis of 1-(quinolin-8-yl)-4-(2-(trifluoromethyl)phenethyl)azetidin-2-one

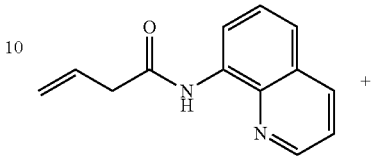

1p

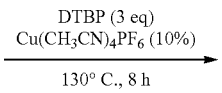

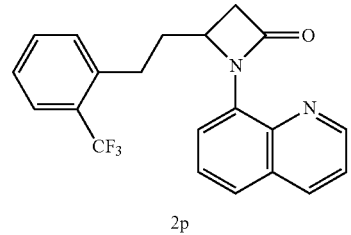

2p

N-(8-quinolyl)-3-butenamide to (0.042 g, 0.2 mmol) and Cu(CH$_3$CN)$_4$PF$_6$ (0.008 g, 0.02 mmol) were weighed and dissolved in p-iodotoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2o. The yield after separation was 52%.

2o: $^1$H NMR (400 MHz, CDCl$_3$) δ 8.76 (dd, J=4.1, 1.8 Hz, 1H), 8.23 (dd, J=7.5, 1.3 Hz, 1H), 8.12 (dd, J=8.3, 1.7 Hz, 1H), 7.58 (dd, J=8.2, 1.3 Hz, 1H), 7.56-7.52 (m, 2H), 7.50 (t, J=7.8 Hz, 1H), 7.40 (dd, J=8.3, 4.1 Hz, 1H), 6.85 (d, J=8.3 Hz, 2H), 5.18 (ddd, J=11.6, 5.6, 3.0 Hz, 1H), 3.32 (dd, J=15.0, 5.3 Hz, 1H), 2.81 (dd, J=15.0, 2.6 Hz, 1H), 2.68-2.54 (m, 2H), 2.32 (tdd, J=9.1, 7.2, 3.3 Hz, 1H), 1.83 (dtd, J=13.5, 8.7, 6.3 Hz, 1H). $^{13}$C NMR (101 MHz, CDCl$_3$) δ 166.29 (s), 148.92 (s), 140.72 (s), 140.58 (s), 137.37 (s), 136.09 (s), 133.51 (s), 130.38 (s), 128.99 (s), 126.73 (s), 124.08 (s), 121.62 (s), 121.37 (s), 91.01 (s), 55.89 (s), 43.04 (s), 34.93 (s), 31.09 (s); HRMS Calcd for C$_{20}$H$_{18}$BrN$_2$O [M+H]$^+$: 429.0464, Found: 429.0472.

N-(8-quinolyl)-3-butenamide 1p (0.042 g, 0.2 mmol) and Cu(CH$_3$CN)$_4$PF$_6$ (0.008 g, 0.02 mmol) were weighed and dissolved in o-trifluoromethyltoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2p. The yield after separation was 76%.

2p: $^1$H NMR (400 MHz, CDCl$_3$) δ 8.81 (dd, J=4.1, 1.7 Hz, 1H), 8.28 (dd, J=7.5, 1.3 Hz, 1H), 8.11 (dd, J=8.3, 1.7 Hz, 1H), 7.60-7.54 (m, 2H), 7.50 (t, J=7.8 Hz, 1H), 7.40 (dd, J=8.3, 4.3 Hz, 2H), 7.23 (dd, J=13.9, 7.4 Hz, 2H), 5.26 (ddd, J=11.7, 5.6, 3.0 Hz, 1H), 3.38 (dd, J=15.0, 5.3 Hz, 1H), 2.88 (dd, J=15.0, 2.6 Hz, 1H), 2.86-2.75 (m, 2H), 2.44-2.30 (m, 1H), 1.92-1.76 (m, 1H). $^{19}$F NMR (376 MHz, CDCl$_3$) δ −59.65 (s). $^{13}$C NMR (101 MHz, CDCl$_3$) δ 166.33 (s), 148.93 (s), 140.54 (s), 140.01 (s), 136.03 (s), 133.58 (s), 131.73 (s), 130.90 (s), 128.99 (s), 128.29 (dd, J=50.2, 20.6 Hz), 126.69 (s), 126.12 (s), 125.96 (q, J=272.0 Hz), 125.96 (d, J=5.7 Hz), 123.99 (s), 121.49 (s), 121.34 (s), 56.12 (s), 43.15 (s), 35.93 (s), 28.44 (s); HRMS Calcd for C$_{21}$H$_{17}$F$_3$N$_2$ONa [M+Na]$^+$: 393.1191, Found: 393.1196.

Example 17

Synthesis of 1-(quinolin-8-yl)-4-(3-(trifluoromethyl)phenethyl)azetidin-2-one

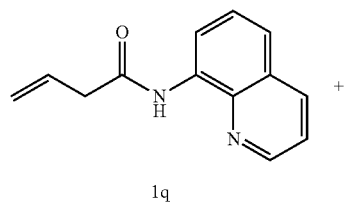

1q

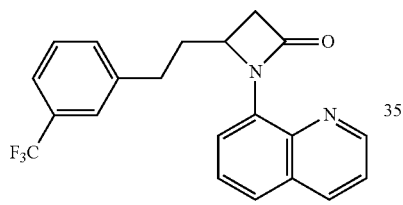

2q

N-(8-quinolyl)-3-butenamide 1q (0.042 g, 0.2 mmol) and Cu(CH$_3$CN)$_4$PF$_6$ (0.008 g, 0.02 mmol) were weighed and dissolved in m-trifluoromethyltoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2q. The yield after separation was 64%.

2q: $^1$H NMR (400 MHz, CDCl$_3$) δ 8.75 (dd, J=4.1, 1.8 Hz, 1H), 8.25 (dd, J=7.5, 1.4 Hz, 1H), 8.12 (dd, J=8.4, 1.7 Hz, 1H), 7.58 (dd, J=8.2, 1.4 Hz, 1H), 7.54-7.47 (m, 1H), 7.43 (d, J=7.8 Hz, 1H), 7.40 (dd, J=8.4, 4.2 Hz, 1H), 7.35 (d, J=7.2 Hz, 2H), 7.29 (d, J=7.4 Hz, 1H), 5.21 (ddd, J=11.7, 5.7, 3.1 Hz, 1H), 3.34 (dd, J=15.0, 5.3 Hz, 1H), 2.83 (dd, J=15.0, 2.6 Hz, 1H), 2.78-2.67 (m, 2H), 2.45-2.33 (m, 1H), 1.89 (dtd, J=13.4, 8.8, 6.2 Hz, 1H). $^{19}$F NMR (376 MHz, CDCl$_3$) δ −62.54 (s). $^{13}$C NMR (101 MHz, CDCl$_3$) δ 166.22 (s), 148.95 (s), 141.98 (s), 140.57 (s), 136.10 (s), 133.47 (s), 131.74 (s), 130.70 (q, J=33.3 Hz), 129.01 (s), 128.80 (s), 126.71 (s), 125.35 (q, J=241.0 Hz), 124.92 (q, J=3.7 Hz), 124.13 (s), 122.94 (dd, J=7.5, 3.6 Hz), 121.64 (s), 121.39 (s), 55.81 (s), 43.07 (s), 34.98 (s), 31.44 (s); HRMS Calcd for C$_{21}$H$_{17}$F$_3$N$_2$ONa [M+Na$^+$]: 393.1191, Found: 393.1198.

Example 18

Synthesis of 1-(quinolin-8-yl)-4-(4-(trifluoromethyl)phenethyl)azetidin-2-one

1r

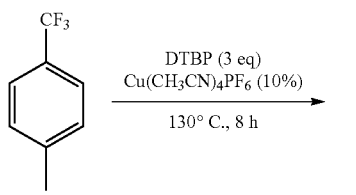

2r

N-(8-quinolyl)-3-butenamide 1r (0.042 g, 0.2 mmol) and Cu(CH$_3$CN)$_4$PF$_6$ (0.008 g, 0.02 mmol) were weighed and dissolved in p-trifluoromethyltoluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 2r. The yield after separation was 48%.

2r: $^1$H NMR (400 MHz, CDCl$_3$) δ 8.75 (dd, J=4.1, 1.7 Hz, 1H), 8.24 (dd, J=7.5, 1.4 Hz, 1H), 8.12 (dd, J=8.3, 1.7 Hz, 1H), 7.58 (dd, J=8.1, 1.3 Hz, 1H), 7.50 (t, J=8.0 Hz, 3H), 7.40 (dd, J=8.3, 4.1 Hz, 1H), 7.21 (d, J=8.1 Hz, 2H), 5.21 (ddd, J=11.6, 5.6, 3.0 Hz, 1H), 3.34 (dd, J=15.0, 5.3 Hz, 1H), 2.84 (dd, J=15.0, 2.6 Hz, 1H), 2.74 (dt, J=14.0, 6.1 Hz, 2H), 2.43-2.32 (m, 1H), 1.90 (dtd, J=13.5, 8.8, 6.3 Hz, 1H). $^{19}$F NMR (376 MHz, CDCl$_3$) δ −62.36 (s). $^{13}$C NMR (101 MHz, CDCl$_3$) δ 166.21 (s), 148.89 (s), 145.24 (s), 140.56 (s), 136.12 (s), 133.48 (s), 129.00 (s), 128.59 (s), 126.73 (s), 125.58 (q, J=268.7 Hz), 125.41 (d, J=4.0 Hz), 125.27 (dd, J=7.6, 3.8 Hz), 124.11 (s), 121.61 (s), 121.37 (s), 55.83 (s), 43.02 (s), 34.88 (s), 31.40 (s); HRMS Calcd for C$_{21}$H$_{18}$F$_3$N$_2$O [M+H$^+$]: 371.1371, Found: 371.1382.

Example 19

Synthesis of 3-methyl-4-phenethyl-1-(quinolin-8-yl)azetidin-2-one

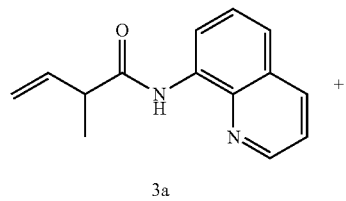

3a

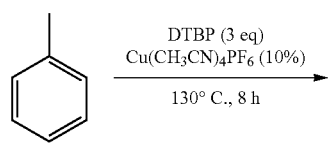

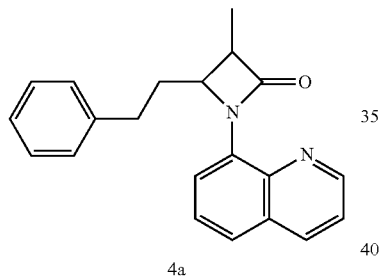

4a

N-(8-quinolyl)-2-methyl-3-butenamide 3a (0.045 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4a. The yield after separation was 85%.

4a: $^1$H NMR (400 MHz, CDCl$_3$) δ 8.77 (dd, J=4.1, 1.7 Hz, 1H), 8.27 (dd, J=7.4, 1.4 Hz, 1H), 8.11 (dd, J=8.3, 1.7 Hz, 1H), 7.56 (dd, J=8.1, 1.3 Hz, 1H), 7.50 (t, J=7.8 Hz, 1H), 7.38 (dd, J=8.3, 4.1 Hz, 1H), 7.26 (dd, J=8.2, 6.6 Hz, 2H), 7.22-7.12 (m, 3H), 4.82 (dt, J=9.6, 2.7 Hz, 1H), 3.03 (qd, J=7.3, 2.2 Hz, 1H), 2.72 (t, J=7.7 Hz, 2H), 2.44-2.32 (m, 1H), 1.95-1.80 (m, 1H), 1.44 (d, J=7.4 Hz, 3H). $^{13}$C NMR (101 MHz, CDCl$_3$) δ 169.54 (s), 148.37 (s), 140.71 (s), 140.15 (s), 135.50 (s), 133.09 (s), 128.53 (s), 127.90 (s), 127.85 (s), 126.23 (s), 125.55 (s), 123.33 (s), 121.20 (s), 120.78 (s), 63.98 (s), 50.68 (s), 34.45 (s), 31.33 (s), 13.26 (s); HRMS Calcd for C$_{21}$H$_{21}$N$_2$O [M+H$^+$]: 317.1654, Found: 317.1645.

Example 20

Synthesis of 3-ethyl-4-phenethyl-1-(quinolin-8-yl)azetidin-2-one

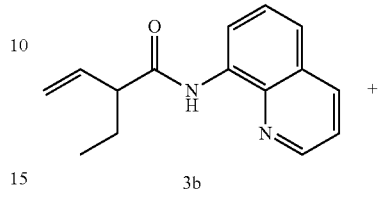

3b

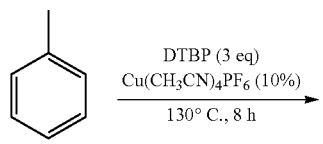

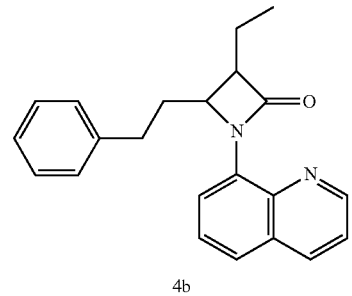

4b

N-(8-quinolyl)-2-ethyl-3-butenamide 3b (0.048 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4b. The yield after separation was 82%.

4b: $^1$H NMR (400 MHz, CDCl$_3$) δ 8.79 (dd, J=4.1, 1.6 Hz, 1H), 8.30 (dd, J=7.4, 0.8 Hz, 1H), 8.11 (dd, J=8.3, 1.5 Hz, 1H), 7.56 (d, J=7.9 Hz, 1H), 7.50 (t, J=7.8 Hz, 1H), 7.39 (dd, J=8.3, 4.1 Hz, 1H), 7.25 (dd, J=9.0, 5.9 Hz, 2H), 7.20-7.11 (m, 3H), 4.93 (dt, J=9.3, 2.6 Hz, 1H), 3.01 (ddd, J=8.2, 6.2, 2.1 Hz, 1H), 2.71 (dd, J=8.6, 5.9 Hz, 2H), 2.46-2.28 (m, 1H), 2.06-1.93 (m, 1H), 1.91-1.80 (m, 2H), 1.15 (t, J=7.4 Hz, 3H). $^{13}$C NMR (101 MHz, CDCl$_3$) δ 169.52 (s), 148.88 (s), 141.26 (s), 140.65 (s), 135.98 (s), 133.59 (s), 129.01 (s), 128.36 (s), 128.25 (s), 126.71 (s), 125.98 (s), 123.80 (s), 121.62 (s), 121.26 (s), 62.46 (s), 58.00 (s), 35.01 (s), 31.78 (s), 22.23 (s), 11.97 (s); HRMS Calcd for C$_{22}$H$_{22}$N$_2$ONa [M+Na]$^+$: 353.1630; Found: 353.1632.

Example 21

Synthesis of 4-phenethyl-3-propyl-1-(quinolin-8-yl)azetidin-2-one

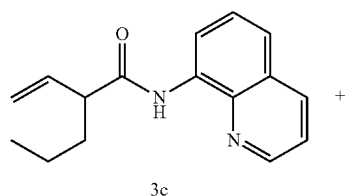

3c

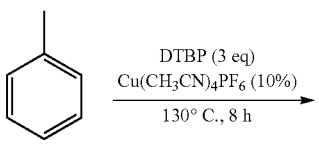

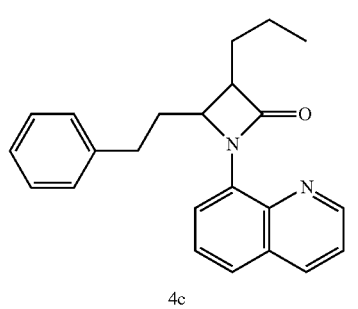

4c

N-(8-quinolyl)-2-propyl-3-butenamide 3c (0.051 g, 0.2 mmol) and Cu(CH₃CN)₄PF₆ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4c. The yield after separation was 75%.

4c: $^1$H NMR (400 MHz, CDCl$_3$) δ 8.79 (dd, J=4.1, 1.8 Hz, 1H), 8.30 (dd, J=7.4, 1.1 Hz, 1H), 8.11 (dd, J=8.4, 1.7 Hz, 1H), 7.56 (dd, J=8.2, 1.5 Hz, 1H), 7.53-7.46 (m, 1H), 7.39 (dd, J=8.3, 4.1 Hz, 1H), 7.26-7.23 (m, 2H), 7.17 (d, J=7.3 Hz, 1H), 7.12 (d, J=7.1 Hz, 2H), 4.92 (dt, J=9.3, 2.7 Hz, 1H), 3.06 (ddd, J=8.4, 6.2, 2.2 Hz, 1H), 2.70 (t, J=8.0 Hz, 2H), 2.44-2.29 (m, 1H), 2.02-1.87 (m, 2H), 1.85-1.75 (m, 1H), 1.66-1.49 (m, 2H), 1.01 (t, J=7.3 Hz, 3H). $^{13}$C NMR (101 MHz, CDCl$_3$) δ 169.65 (s), 148.86 (s), 141.28 (s), 140.66 (s), 135.98 (s), 133.62 (s), 129.01 (s), 128.36 (s), 128.24 (s), 126.72 (s), 125.97 (s), 123.78 (s), 121.62 (s), 121.25 (s), 62.96 (s), 56.44 (s), 35.04 (s), 31.74 (s), 31.33 (s), 20.86 (s), 14.16 (s); HRMS Calcd for C$_{23}$H$_{25}$N$_2$O [M+H]$^+$: 345.1967, Found: 345.1972.

Example 22

Synthesis of 3-isopropyl-4-phenethyl-1-(quinolin-8-yl)azetidin-2-one

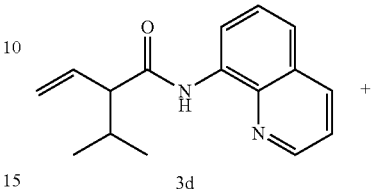

3d

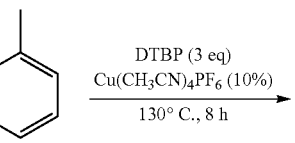

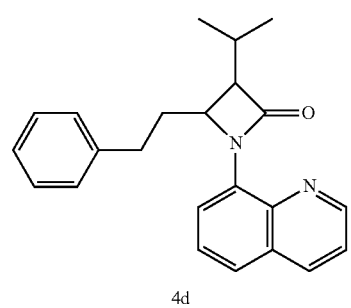

4d

N-(8-quinolyl)-2-isopropyl-3-butenamide 3d (0.051 g, 0.2 mmol) and Cu(CH₃CN)₄PF₆ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4d. The yield after separation was 73%.

4d: $^1$H NMR (400 MHz, CDCl$_3$) δ 8.82 (dd, J=4.1, 1.7 Hz, 1H), 8.32 (dd, J=7.4, 1.4 Hz, 1H), 8.11 (dd, J=8.3, 1.7 Hz, 1H), 7.56 (dd, J=8.1, 1.4 Hz, 1H), 7.50 (t, J=7.8 Hz, 1H), 7.39 (dd, J=8.3, 4.1 Hz, 1H), 7.24 (t, J=7.4 Hz, 2H), 7.18-7.10 (m, 3H), 5.05-5.00 (m, 1H), 2.91 (dd, J=7.8, 2.2 Hz, 1H), 2.70 (t, J=8.2 Hz, 2H), 2.38-2.28 (m, 1H), 2.22 (dq, J=13.7, 6.8 Hz, 1H), 1.95-1.83 (m, 1H), 1.22 (d, J=6.7 Hz, 3H), 1.15 (d, J=6.7 Hz, 3H). $^{13}$C NMR (101 MHz, CDCl$_3$) δ 169.03 (s), 148.91 (s), 141.36 (s), 140.76 (s), 135.98 (s), 133.59 (s), 129.02 (s), 128.35 (s), 128.19 (s), 126.71 (s), 125.94 (s), 123.82 (s), 121.64 (s), 121.26 (s), 63.29 (s), 60.70 (s), 35.13 (s), 31.75 (s), 28.48 (s), 20.97 (s), 20.45 (s); HRMS Calcd for C$_{23}$H$_{25}$N$_2$O [M+H]$^+$: 345.1967, Found: 345.1977.

Example 23

Synthesis of 3,3-dimethyl-4-phenethyl-1-(quinolin-8-yl)azetidin-2-one

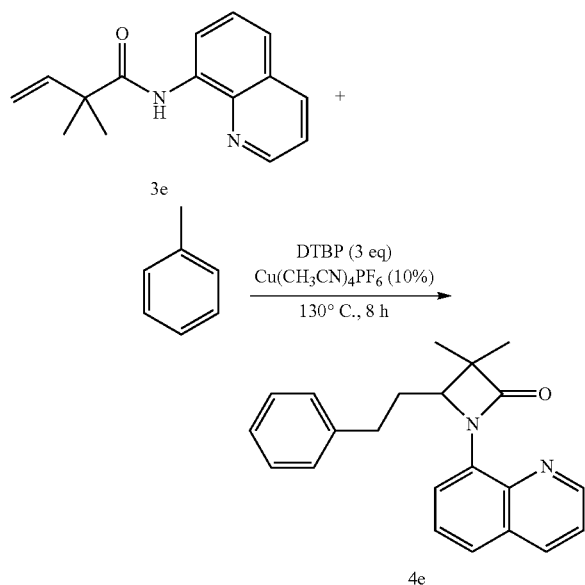

N-(8-quinolyl)-2,2'-dimethyl-3-butenamide 3e (0.048 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4e. The yield after separation was 52%.

4e: $^1$H NMR (400 MHz, CDCl$_3$) δ 8.75 (dd, J=4.1, 1.8 Hz, 1H), 8.17 (dd, J=7.5, 1.4 Hz, 1H), 8.09 (dd, J=8.3, 1.7 Hz, 1H), 7.56 (dd, J=8.2, 1.4 Hz, 1H), 7.54-7.44 (m, 1H), 7.37 (dd, J=8.3, 4.1 Hz, 1H), 7.25 (td, J=6.9, 1.8 Hz, 2H), 7.22-7.16 (m, 1H), 7.13-7.06 (m, 2H), 4.91 (dd, J=9.8, 3.7 Hz, 1H), 2.74-2.55 (m, 2H), 2.33-2.14 (m, 1H), 1.98-1.80 (m, 1H), 1.52 (s, 3H), 1.38 (s, 3H). $^{13}$C NMR (101 MHz, CDCl$_3$) δ 172.83 (s), 148.48 (s), 141.01 (s), 140.66 (s), 135.50 (s), 132.83 (s), 128.57 (s), 127.91 (s), 127.90 (s), 126.17 (s), 125.54 (s), 123.75 (s), 122.21 (s), 120.80 (s), 67.26 (s), 52.59 (s), 32.31 (s), 31.17 (s), 23.03 (s), 16.64 (s); HRMS Calcd for C$_{22}$H$_{22}$N$_2$ONa [M+Na]$^+$: 353.1630, Found: 353.1643.

Example 24

Synthesis of 3-allyl-4-phenethyl-1-(quinolin-8-yl)azetidin-2-one

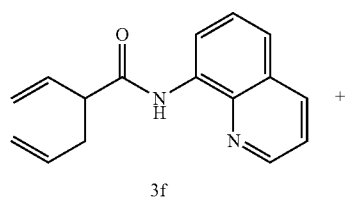

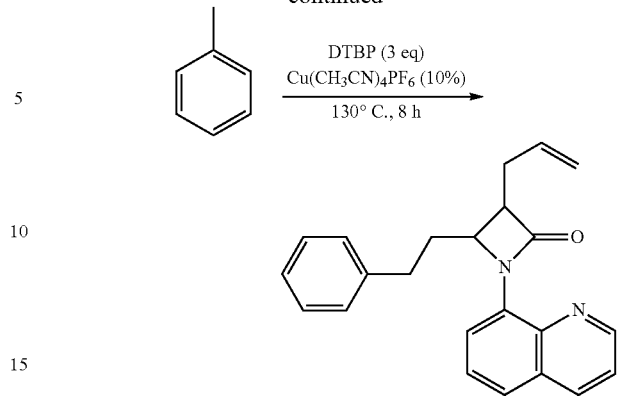

N-(8-quinolyl)-2-allyl-3-butenamide 3f (0.051 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4f. The yield after separation was 79%.

4f: $^1$H NMR (400 MHz, CDCl$_3$) δ 8.78 (dd, J=4.1, 1.7 Hz, 1H), 8.30 (dd, J=7.5, 1.4 Hz, 1H), 8.11 (dd, J=8.3, 1.7 Hz, 1H), 7.57 (dd, J=8.1, 1.4 Hz, 1H), 7.50 (t, J=7.8 Hz, 1H), 7.39 (dd, J=8.3, 4.1 Hz, 1H), 7.30-7.21 (m, 2H), 7.18 (d, J=7.3 Hz, 1H), 7.15-7.10 (m, 2H), 5.96 (ddt, J=17.1, 10.1, 7.0 Hz, 1H), 5.24 (dd, J=17.0, 1.5 Hz, 1H), 5.15 (d, J=10.1 Hz, 1H), 4.95 (dt, J=9.3, 2.8 Hz, 1H), 3.27-2.87 (m, 1H), 2.88-2.64 (m, 3H), 2.63-2.49 (m, 1H), 2.36 (tdd, J=9.3, 7.2, 3.2 Hz, 1H), 1.88 (dtd, J=13.4, 8.9, 6.7 Hz, 1H). $^{13}$C NMR (101 MHz, CDCl$_3$) δ 168.75 (s), 148.93 (s), 141.26 (s), 140.63 (s), 135.98 (s), 134.99 (s), 133.52 (s), 129.01 (s), 128.36 (s), 128.29 (s), 126.69 (s), 125.99 (s), 123.92 (s), 121.65 (s), 121.29 (s), 117.38 (s), 62.41 (s), 56.00 (s), 34.91 (s), 33.31 (s), 31.78 (s); HRMS Calcd for C$_{23}$H$_{23}$N$_2$O [M+H]$^+$: 343.1810, Found: 343.1810.

Example 25

Synthesis of 3-benzyl-4-phenethyl-1-(quinolin-8-yl)azetidin-2-one

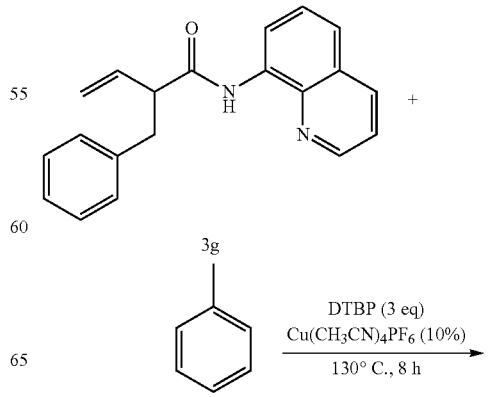

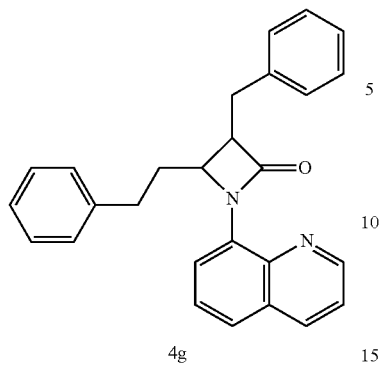

4g

N-(8-quinolyl)-2-benzyl-3-butenamide 3g (0.061 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4g. The yield after separation was 84%.

4g: $^1$H NMR (400 MHz, CDCl$_3$) δ 8.68 (dd, J=4.1, 1.8 Hz, 1H), 8.20 (dd, J=7.5, 1.5 Hz, 1H), 8.00 (dd, J=8.3, 1.7 Hz, 1H), 7.47 (dd, J=8.1, 1.3 Hz, 1H), 7.43-7.37 (m, 1H), 7.33-7.22 (m, 5H), 7.20-7.13 (m, 1H), 7.11-7.06 (m, 2H), 7.03 (dd, J=4.9, 3.5 Hz, 1H), 6.85-6.74 (m, 2H), 4.89 (dt, J=9.6, 2.4 Hz, 1H), 3.32-3.13 (m, 2H), 2.94 (dd, J=13.3, 9.4 Hz, 1H), 2.24-2.17 (m, 1H), 2.17-2.03 (m, 2H), 1.66 (ddt, J=10.5, 9.3, 8.0 Hz, 1H). $^{13}$C NMR (101 MHz, CDCl$_3$) δ 168.74 (s), 148.98 (s), 141.29 (s), 140.68 (s), 139.20 (s), 136.00 (s), 133.47 (s), 129.02 (s), 128.71 (s), 128.26 (s), 128.15 (s), 126.70 (s), 126.65 (s), 125.85 (s), 124.05 (s), 121.79 (s), 121.32 (s), 62.93 (s), 58.37 (s), 35.35 (s), 34.79 (s), 31.20 (s); HRMS Calcd for C$_{27}$H$_{25}$N$_2$O [M+H]$^+$: 393.1967, Found: 393.1967.

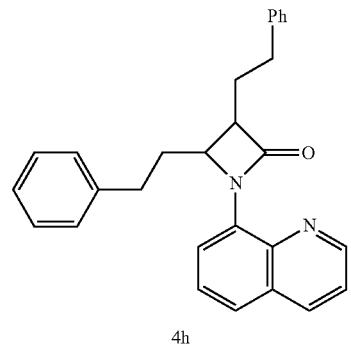

4h

N-(8-quinolyl)-2-phenylethyl-3-butenamide 3h (0.063 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4h. The yield after separation was 80%.

4h: $^1$H NMR (400 MHz, CDCl$_3$) δ 8.76 (dd, J=4.1, 1.8 Hz, 1H), 8.24 (dd, J=7.5, 1.5 Hz, 1H), 8.07 (dd, J=8.3, 1.7 Hz, 1H), 7.53 (dd, J=8.2, 1.4 Hz, 1H), 7.50-7.42 (m, 1H), 7.35 (dd, J=8.3, 4.1 Hz, 1H), 7.26 (d, J=7.2 Hz, 2H), 7.23 (t, J=2.2 Hz, 2H), 7.21 (d, J=4.2 Hz, 2H), 7.18 (dd, J=4.5, 2.4 Hz, 1H), 7.13 (d, J=7.3 Hz, 1H), 7.08-7.04 (m, 2H), 4.99-4.89 (m, 1H), 3.03 (td, J=7.8, 2.2 Hz, 1H), 2.94-2.75 (m, 2H), 2.63 (t, J=7.9 Hz, 2H), 2.35-2.18 (m, 2H), 2.15-2.03 (m, 1H), 1.89-1.75 (m, 1H). $^{13}$C NMR (101 MHz, CDCl$_3$) δ 169.27 (s), 148.92 (s), 141.44 (s), 141.15 (s), 140.71 (s), 136.00 (s), 133.52 (s), 129.02 (s), 128.59 (s), 128.49 (s), 128.46 (s), 128.38 (s), 128.26 (s), 126.72 (s), 126.02 (s), 123.92 (s), 121.72 (s), 121.29 (s), 62.90 (s), 55.84 (s), 34.83 (s), 33.58 (s), 31.70 (s), 30.92 (s); HRMS Calcd for C$_{28}$H$_{27}$N$_2$O [M+H]$^+$: 407.2123, Found: 407.2134.

Example 26

Synthesis of 3,4-diphenethyl-1-(quinolin-8-yl)azetidin-2-one

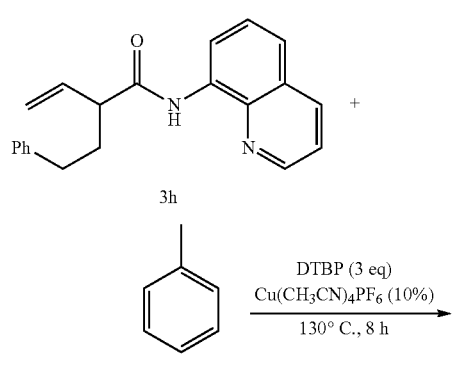

Example 27

Synthesis of 3-(cyclopropylmethyl)-4-phenethyl-1-(quinolin-8-yl)azetidin-2-one

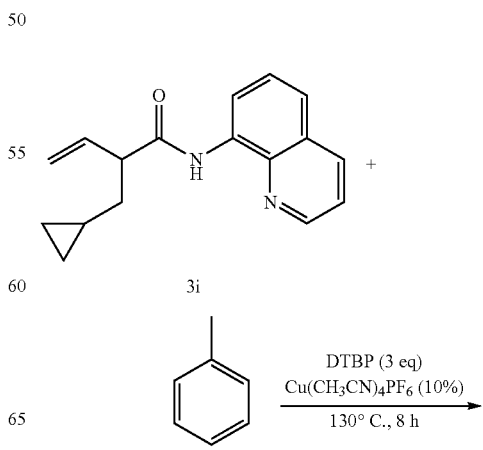

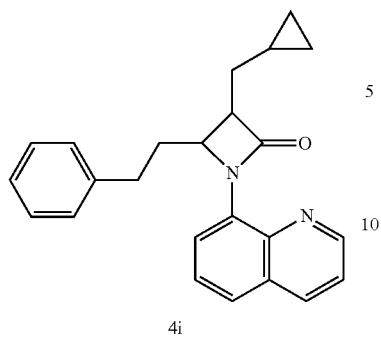

4i

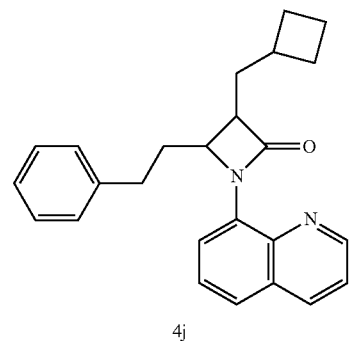

4j

N-(8-quinolyl)-2-methylcyclopropane-3-butenamide 3i (0.053 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4i. The yield after separation was 78%.

4i: $^1$H NMR (400 MHz, CDCl$_3$) δ 8.81 (dd, J=4.1, 1.8 Hz, 1H), 8.30 (dd, J=7.4, 1.4 Hz, 1H), 8.11 (dd, J=8.3, 1.8 Hz, 1H), 7.56 (dd, J=8.2, 1.5 Hz, 1H), 7.53-7.47 (m, 1H), 7.39 (dd, J=8.3, 4.1 Hz, 1H), 7.27-7.24 (m, 2H), 7.20-7.11 (m, 3H), 5.11-4.96 (m, 1H), 3.15 (ddd, J=8.4, 6.2, 2.2 Hz, 1H), 2.80-2.71 (m, 2H), 2.45-2.33 (m, 1H), 1.89 (ddd, J=13.1, 6.5, 3.3 Hz, 1H), 1.82-1.77 (m, 2H), 0.94 (tdd, J=7.6, 5.0, 2.6 Hz, 1H), 0.54 (dd, J=8.1, 1.4 Hz, 2H), 0.20 (ddd, J=16.1, 7.5, 3.1 Hz, 2H). $^{13}$C NMR (101 MHz, CDCl$_3$) δ 169.47 (s), 148.89 (s), 141.34 (s), 140.68 (s), 135.99 (s), 133.62 (s), 129.03 (s), 128.37 (s), 128.23 (s), 126.72 (s), 125.98 (s), 123.82 (s), 121.65 (s), 121.27 (s), 62.77 (s), 56.96 (s), 35.10 (s), 34.00 (s), 31.79 (s), 9.25 (s), 5.11 (s), 4.55 (s); HRMS Calcd for C$_{24}$H$_{24}$N$_2$ONa [M+H]$^+$: 379.1786, Found: 379.1769.

N-(8-quinolyl)-2-methylcyclobutane-3-butenamide 3j (0.055 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4j. The yield after separation was 75%.

4j: $^1$H NMR (400 MHz, CDCl$_3$) δ 8.80 (dd, J=4.1, 1.7 Hz, 1H), 8.28 (dd, J=7.4, 1.4 Hz, 1H), 8.11 (dd, J=8.3, 1.7 Hz, 1H), 7.56 (dd, J=8.1, 1.4 Hz, 1H), 7.53-7.47 (m, 1H), 7.39 (dd, J=8.3, 4.1 Hz, 1H), 7.25 (dd, J=9.0, 5.7 Hz, 2H), 7.19-7.11 (m, 3H), 4.97-4.88 (m, 1H), 2.97 (ddd, J=8.4, 6.0, 2.1 Hz, 1H), 2.68 (t, J=8.0 Hz, 2H), 2.57 (dt, J=15.4, 7.8 Hz, 1H), 2.33 (dtd, J=11.3, 8.2, 3.2 Hz, 1H), 2.15 (dtd, J=11.5, 7.6, 3.6 Hz, 2H), 2.05 (ddd, J=14.2, 8.4, 6.1 Hz, 1H), 1.96-1.90 (m, 2H), 1.89-1.83 (m, 2H), 1.76-1.68 (m, 2H). $^{13}$C NMR (101 MHz, CDCl$_3$) δ 169.72 (s), 148.87 (s), 141.29 (s), 140.68 (s), 135.98 (s), 133.62 (s), 129.01 (s), 128.38 (s), 128.22 (s), 126.71 (s), 125.99 (s), 123.81 (s), 121.65 (s), 121.26 (s), 62.89 (s), 54.75 (s), 36.26 (s), 35.05 (s), 34.12 (s), 31.67 (s), 28.51 (s), 28.37 (s), 18.44 (s); HRMS Calcd for C$_{25}$H$_{27}$N$_2$O [M+H]$^+$: 371.2123, Found: 371.2125.

Example 28

Synthesis of 3-(cyclobutylmethyl)-4-phenethyl-1-(quinolin-8-yl)azetidin-2-one

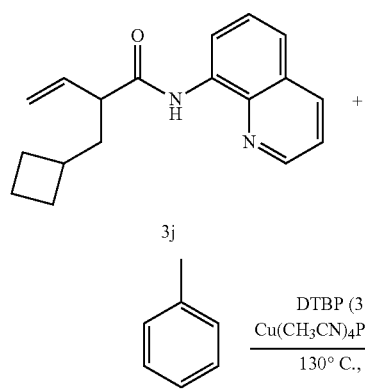

3j $\xrightarrow[\text{130° C., 8 h}]{\text{DTBP (3 eq)}\ \text{Cu(CH}_3\text{CN)}_4\text{PF}_6\ (10\%)}$ Example 29

Synthesis of 4-(1-phenylpropan-2-yl)-1-(quinolin-8-yl)azetidin-2-one

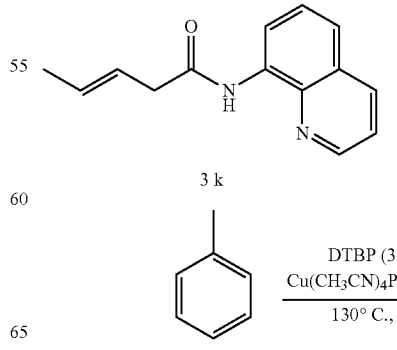

3k $\xrightarrow[\text{130° C., 8 h}]{\text{DTBP (3 eq)}\ \text{Cu(CH}_3\text{CN)}_4\text{PF}_6\ (10\%)}$

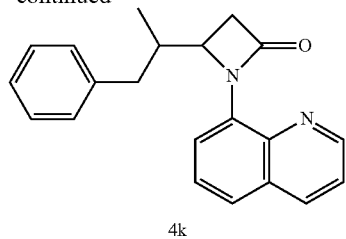

4k

N-(8-quinolyl)-3-pentenamide 3k (0.045 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4k. The yield after separation was 40%.

4k: $^1$H NMR (400 MHz, CDCl$_3$) δ 8.86 (dd, J=4.1, 1.7 Hz, 1H), 8.14 (ddd, J=8.7, 7.9, 1.5 Hz, 2H), 7.64 (dd, J=8.2, 1.2 Hz, 1H), 7.53 (t, J=7.8 Hz, 1H), 7.42 (dd, J=8.3, 4.2 Hz, 1H), 7.08 (t, J=4.9 Hz, 3H), 6.81-6.75 (m, 2H), 5.24 (td, J=5.2, 2.7 Hz, 1H), 3.25 (dd, J=15.2, 5.6 Hz, 1H), 2.96 (dd, J=15.2, 2.7 Hz, 1H), 2.80 (dd, J=12.9, 3.4 Hz, 1H), 2.35-2.27 (m, 1H), 2.22 (dd, J=12.9, 10.3 Hz, 1H), 0.82 (d, J=6.6 Hz, 3H). $^{13}$C NMR (101 MHz, CDCl$_3$) δ 166.69 (s), 149.18 (s), 141.52 (s), 140.25 (s), 136.09 (s), 133.92 (s), 129.03 (s), 128.83 (s), 128.13 (s), 126.71 (s), 125.81 (s), 124.68 (s), 122.84 (s), 121.40 (s), 60.38 (s), 39.40 (s), 37.52 (s), 36.87 (s), 15.66 (s); HRMS Calcd for C$_{21}$H$_{20}$N$_2$ONa [M+Na]$^+$: 339.1473, Found: 339.1468.

Example 30

Synthesis of 4-(1-phenylbutan-2-yl)-1-(quinolin-8-yl)azetidin-2-one

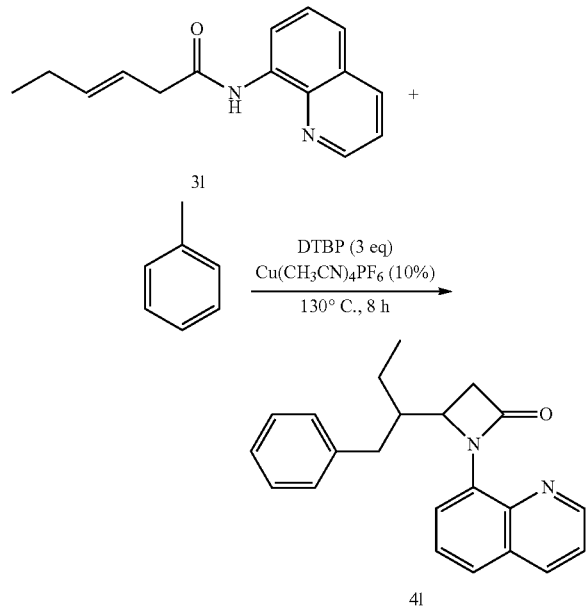

N-(8-quinolyl)-3-hexenamide 31 (0.048 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4l. The yield after separation was 20%.

4l: $^1$H NMR (400 MHz, CDCl$_3$) δ 8.84 (dd, J=4.1, 1.8 Hz, 1H), 8.17-8.12 (m, 2H), 7.62 (dd, J=8.2, 1.3 Hz, 1H), 7.50 (dd, J=10.3, 5.4 Hz, 1H), 7.42 (dd, J=8.3, 4.1 Hz, 1H), 7.05-7.00 (m, 3H), 6.71-6.67 (m, 2H), 5.45 (td, J=5.7, 3.0 Hz, 1H), 3.21 (dd, J=15.2, 5.6 Hz, 1H), 3.00 (dd, J=15.2, 2.8 Hz, 1H), 2.76 (dd, J=13.4, 4.0 Hz, 1H), 2.35 (dd, J=13.4, 9.7 Hz, 1H), 2.22 (ddt, J=12.3, 8.4, 4.1 Hz, 1H), 1.42 (dtd, J=12.2, 7.5, 4.7 Hz, 1H), 1.24-1.18 (m, 1H), 0.93 (t, J=7.5 Hz, 3H). $^{13}$C NMR (101 MHz, CDCl$_3$) δ 166.19 (s), 148.55 (s), 140.65 (s), 140.10 (s), 135.60 (s), 133.25 (s), 128.48 (s), 128.31 (s), 127.59 (s), 126.30 (s), 125.19 (s), 123.82 (s), 121.87 (s), 120.90 (s), 57.72 (s), 41.94 (s), 38.23 (s), 33.56 (s), 23.04 (s), 11.03 (s); HRMS Calcd for C$_{22}$H$_{23}$N$_2$O [M+H$^+$]: 331.1810, Found: 331.1813.

Example 31

Synthesis of 4-(1,3-diphenylpropan-2-yl)-1-(quinolin-8-yl)azetidin-2-one

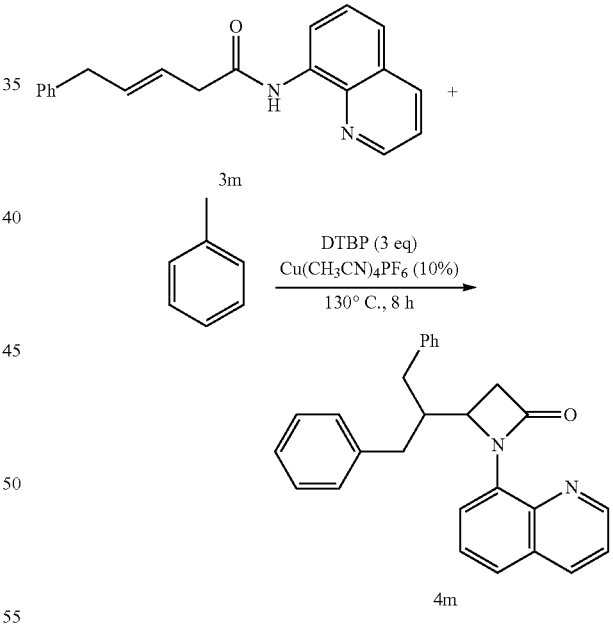

Compound 3m (0.060 g, 0.2 mmol) and Cu(CH$_3$CN)$_4$PF$_6$ (0.008 g, 0.02 mmol) were weighed and dissolved in toluene (1 mL), and DTBP (0.088 g, 0.6 mmol) was added. The mixture was heated to 130° C. and reacted until the reaction was completed as indicated by TLC. After the reaction, the crude product was separated and purified by column chromatography on silica gel (petroleum ether:ethyl acetate=10:1) to obtain the compound 4m. The yield after separation was 20%.

4m: $^1$H NMR (400 MHz, CDCl$_3$) δ 8.54 (dd, J=4.1, 1.8 Hz, 1H), 8.12 (ddd, J=5.1, 3.1, 1.6 Hz, 2H), 7.57 (dd, J=8.2, 1.3 Hz, 1H), 7.49-7.44 (m, 1H), 7.37 (dd, J=8.3, 4.1 Hz, 1H), 7.33-7.28 (m, 2H), 7.22 (dd, J=5.9, 3.5 Hz, 1H), 7.10 (d, J=6.9 Hz, 2H), 7.06-7.00 (m, 3H), 6.71 (dd, J=7.0, 2.4 Hz, 2H), 5.27 (dt, J=5.7, 3.0 Hz, 1H), 3.15 (dd, J=15.2, 5.6 Hz, 1H), 3.01 (dd, J=15.2, 2.9 Hz, 1H), 2.87-2.79 (m, 2H), 2.77 (d, J=4.1 Hz, 1H), 2.45-2.36 (m, 2H). $^{13}$C NMR (101 MHz, CDCl$_3$) δ 166.30 (s), 148.74 (s), 140.65 (s), 140.13 (s), 139.82 (s), 135.96 (s), 133.72 (s), 129.01 (s), 128.83 (s), 128.74 (s), 128.29 (s), 128.20 (s), 126.79 (s), 126.15 (s), 125.84 (s), 123.95 (s), 121.67 (s), 121.27 (s), 57.88 (s), 42.61 (s), 38.28 (s), 37.34 (s), 34.08 (s); HRMS Calcd for $C_{27}H_{25}N_2O$ [M+H$^+$]: 393.1967, Found: 393.1972.

In summary, the present invention discloses a method for preparing a β-lactam derivative, in which a substituted N-quinoline-3-butenamide derivative is used as a substrate to react with toluene, a toluene derivative or a heterocyclic derivative at 90-150° C. in the presence of DTBP and a copper salt, to prepare a variety of β-lactam derivatives with a high yield.

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A method for preparing a β-lactam derivative, comprising the steps of:
reacting a substituted N-quinoline-3-butenamide derivative of Formula (1) and a toluene derivative of Formula (2) at 90-150° C. in the presence of di-tert-butyl peroxide and a copper salt catalyst, to give a β-lactam derivative of Formula (4), where the reaction route is as follows:

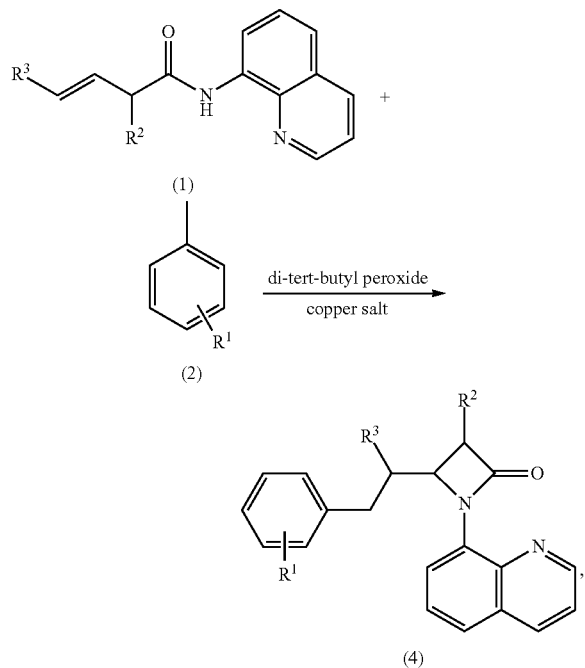

or reacting a substituted N-quinoline-3-butenamide derivative of Formula (1) and a heterocyclic derivative of Formula (3) at 90-150° C. in the presence of di-tert-butyl peroxide and a copper salt catalyst, to give a β-lactam derivative of Formula (5), where the reaction route is as follows:

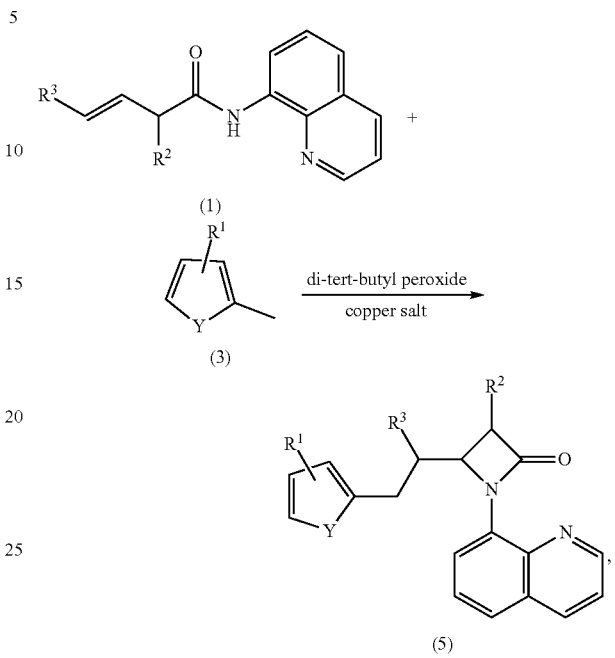

wherein in Formulas (1)-(5), Y is an oxygen or sulfur atom; and
R$^2$ and R$^3$ are hydrogen, and R$^1$ is hydrogen, methyl, halo or trifluoromethyl;
or R$^1$ and R$^2$ are hydrogen, and R$^3$ is C$_1$-C$_6$ alkyl or benzyl;
or R$^1$ and R$^3$ are hydrogen, and R$^2$ is C$_1$-C$_6$ alkyl, allyl, benzyl, phenylethyl, cyclopropylmethyl, or cyclobutylmethyl.

2. The method according to claim 1, wherein the copper salt catalyst is selected from the group consisting of cuprous bromide, copper acetate, cuprous chloride, tetrakis(acetonitrile)copper hexafluorophosphate, copper trifluoromethanesulfonate, copper oxide, copper bromide and any combination thereof.

3. The method according to claim 1, wherein the molar ratio of the substituted N-quinoline-3-butenamide derivative: di-tert-butyl peroxide:copper salt catalyst=1:1-3:0.05-0.2.

4. The method according to claim 1, wherein the copper salt catalyst is tetrakis(acetonitrile)copper hexafluorophosphate.

5. The method according to claim 1, wherein the molar ratio of the substituted N-quinoline-3-butenamide derivative: di-tert-butyl peroxide:copper salt catalyst=1:3:0.05-0.2.

6. The method according to claim 1, wherein the reaction temperature is 130 to 150° C.

7. The method according to claim 1, wherein the reaction system also comprises, in addition to the toluene derivative of Formula (2) or the heterocyclic derivative of Formula (3), an additional organic solvent.

8. The method according to claim 7, wherein the organic solvent is selected from the group consisting of acetonitrile, tetrahydrofuran, N,N-dimethylformamide, isopropanol and any combination thereof.

* * * * *